US008153137B2

(12) United States Patent
Kale

(10) Patent No.: US 8,153,137 B2
(45) Date of Patent: *Apr. 10, 2012

(54) METHODS OF AND SYSTEMS FOR ISOLATING CAROTENOIDS AND OMEGA-3 RICH OIL PRODUCTS FROM ALGAE

(75) Inventor: Aniket Kale, Chandler, AZ (US)

(73) Assignee: Heliae Development, LLC, Gilbert, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/268,064

(22) Filed: Oct. 7, 2011

(65) Prior Publication Data
US 2012/0029184 A1 Feb. 2, 2012

Related U.S. Application Data

(63) Continuation of application No. 13/081,221, filed on Apr. 6, 2011, now Pat. No. 8,084,038.

(60) Provisional application No. 61/321,290, filed on Apr. 6, 2010, provisional application No. 61/321,286, filed on Apr. 6, 2010.

(51) Int. Cl.
*A61K 36/00* (2006.01)
*A61K 36/02* (2006.01)

(52) U.S. Cl. .................................. 424/195.17; 424/725

(58) Field of Classification Search ........................ None
See application file for complete search history.

(56) References Cited

U.S. PATENT DOCUMENTS

| 4,062,882 A | 12/1977 | Sen Gupta |
| 4,190,538 A | 2/1980 | Chen |
| 4,264,452 A | 4/1981 | Chen |
| 4,787,981 A | 11/1988 | Tanahashi et al. |
| 4,925,557 A | 5/1990 | Ahlberg, Jr. et al. |
| 5,130,242 A | 7/1992 | Barclay |
| 5,338,673 A | 8/1994 | Thepenier et al. |
| 5,374,657 A | 12/1994 | Kyle |
| 5,440,028 A | 8/1995 | Buchholz et al. |
| 5,539,133 A | 7/1996 | Kohn et al. |
| 5,545,329 A | 8/1996 | LaMonica |
| 5,658,767 A | 8/1997 | Kyle |
| 6,166,091 A | 12/2000 | Kojima et al. |
| 6,166,231 A | 12/2000 | Hoeksema |
| 6,372,460 B1 | 4/2002 | Gladue et al. |
| 6,441,208 B2 | 8/2002 | Bijl et al. |
| 6,524,486 B2 | 2/2003 | Borodyanski et al. |
| 6,579,714 B1 | 6/2003 | Hirabayashi et al. |
| 6,727,373 B2 | 4/2004 | Bijl et al. |
| 6,750,048 B2 | 6/2004 | Ruecker et al. |
| 6,818,239 B2 | 11/2004 | Kagan et al. |
| 7,015,014 B2 | 3/2006 | Schaap et al. |
| 7,148,366 B2 | 12/2006 | Cheryan |
| 7,575,768 B2 | 8/2009 | Perlman et al. |
| 7,608,270 B2 | 10/2009 | Beckett et al. |
| 7,678,931 B2 | 3/2010 | Fichtali et al. |
| 7,695,626 B2 | 4/2010 | Dueppen et al. |
| 7,816,570 B2 | 10/2010 | Roberts, IV et al. |
| 7,868,195 B2 | 1/2011 | Fleischer et al. |
| 7,883,882 B2 | 2/2011 | Franklin et al. |
| 2002/0009493 A1 | 1/2002 | Schwendeman et al. |
| 2003/0054070 A1 | 3/2003 | Bridges et al. |
| 2004/0131580 A1 | 7/2004 | Hagino et al. |
| 2005/0164192 A1 | 7/2005 | Graham et al. |
| 2005/0170479 A1 | 8/2005 | Weaver et al. |
| 2006/0122410 A1 | 6/2006 | Fichtali et al. |
| 2006/0280840 A1 | 12/2006 | Robertson |
| 2007/0025976 A1 | 2/2007 | Kluetz et al. |
| 2007/0122493 A1 | 5/2007 | Funayama et al. |
| 2007/0196383 A1* | 8/2007 | Murakami et al. ....... 424/195.17 |
| 2007/0196893 A1 | 8/2007 | Weiss et al. |
| 2007/0264271 A1* | 11/2007 | ElSohly et al. ............ 424/184.1 |
| 2008/0038290 A1 | 2/2008 | Renimel et al. |
| 2008/0118964 A1 | 5/2008 | Huntley et al. |
| 2008/0155888 A1 | 7/2008 | Vick et al. |
| 2008/0160593 A1 | 7/2008 | Oyler |

(Continued)

FOREIGN PATENT DOCUMENTS

CA 2 249 103 4/1999

(Continued)

OTHER PUBLICATIONS

Fajardo et al, Lipid extraction from the microalga *Phaeodactylum tricornutum*, European Journal of Lipid Science and Technology (2007) vol. 109, No. 2, pp. 120-126.*
"Algae Oil Extraction," Diversified Technologies, Inc., Bioscience Technology, Jan. 3, 2011 New Source Web Content—US, 1 page.
Agboola, S. et al., "Characterisation and functional properties of Australian rice protein isolates," Journal of Cereal Science 41 (2005), pp. 283-290.
Amin, S. "Review on biofuel oil and gas production processes from microalgae," Energy Conversion and Management 50 (2009), pp. 1834-1840.
Berberoglu, H. et al., "Radiation characteristics of *Chiamydomonas reinhardtii* CC125 and its truncated chlorophyll antenna transformants tla1, tlaX and tla1-CW+"International Journal of Hydrogen Energy 33 (2008), pp. 6467-6483.

(Continued)

*Primary Examiner* — Qiuwen Mi
(74) *Attorney, Agent, or Firm* — Tom Gallegos, Esq.; Colleen M. Superko, Esq.

(57) ABSTRACT

A method of isolating nutraceuticals products from algae is provided. A method of isolating carotenoids and omega-3 rich oil from algae includes dewatering substantially intact algal cells to make an algal biomass and adding a first ethanol fraction to the algal biomass. The method also includes separating a first substantially solid biomass fraction from a first substantially liquid fraction comprising proteins and combining the first substantially solid biomass fraction with a second ethanol fraction. The method further includes separating a second substantially solid biomass fraction from a second substantially liquid fraction comprising polar lipids and combining the second substantially solid biomass fraction with a third ethanol solvent fraction. The method also includes separating a third substantially solid biomass fraction from a third substantially liquid fraction comprising neutral lipids, wherein the third substantially solid biomass fraction comprises carbohydrates and separating the neutral lipids into carotenoids and omega-3 rich oil.

8 Claims, 25 Drawing Sheets

U.S. PATENT DOCUMENTS

| | | |
|---|---|---|
| 2008/0163543 A1 | 7/2008 | Abhari et al. |
| 2009/0029445 A1 | 1/2009 | Eckelberry et al. |
| 2009/0049739 A1 | 2/2009 | Morgan |
| 2009/0056201 A1 | 3/2009 | Morgan |
| 2009/0071064 A1 | 3/2009 | Machacek et al. |
| 2009/0148918 A1 | 6/2009 | Trimbur et al. |
| 2009/0148931 A1 | 6/2009 | Wilkerson et al. |
| 2009/0162919 A1 | 6/2009 | Radaelli et al. |
| 2009/0170801 A1 | 7/2009 | Hao |
| 2009/0181463 A1 | 7/2009 | Chen |
| 2009/0234146 A1 | 9/2009 | Cooney et al. |
| 2010/0055741 A1 | 3/2010 | Galvez, III et al. |
| 2010/0068772 A1 | 3/2010 | Downey |
| 2010/0077654 A1 | 4/2010 | Wu et al. |
| 2010/0081835 A1 | 4/2010 | Wu et al. |
| 2010/0120104 A1 | 5/2010 | Reed |
| 2010/0170144 A1 | 7/2010 | Day et al. |
| 2010/0233761 A1 | 9/2010 | Czartoski et al. |
| 2010/0239712 A1 | 9/2010 | Brooks et al. |
| 2010/0255541 A1 | 10/2010 | Hu et al. |
| 2010/0261922 A1 | 10/2010 | Fleischer et al. |
| 2010/0297331 A1 | 11/2010 | Brooks et al. |
| 2010/0297749 A1 | 11/2010 | Aravanis et al. |
| 2010/0317088 A1 | 12/2010 | Radaelli et al. |
| 2011/0003331 A1 | 1/2011 | Pavia |
| 2011/0086386 A1 | 4/2011 | Czartoski et al. |
| 2011/0124034 A1 | 5/2011 | Kuehnle et al. |
| 2011/0143012 A1 | 6/2011 | Rettenmaier |
| 2011/0182930 A1 | 7/2011 | Erlanson-Albertsson et al. |
| 2011/0192073 A1 | 8/2011 | Kale |
| 2011/0192075 A1 | 8/2011 | Kale |
| 2011/0195085 A1 | 8/2011 | Kale |
| 2011/0195484 A1 | 8/2011 | Kale |
| 2011/0195485 A1 | 8/2011 | Kale |
| 2011/0196131 A1 | 8/2011 | Kale |
| 2011/0196132 A1 | 8/2011 | Kale |
| 2011/0196135 A1 | 8/2011 | Kale |
| 2011/0263886 A1 | 10/2011 | Kale |

FOREIGN PATENT DOCUMENTS

| | | |
|---|---|---|
| EP | 1 057 833 A1 | 12/2000 |
| EP | 1 299 003 B1 | 12/2006 |
| EP | 1 920 777 A1 | 5/2008 |
| EP | 2 030 626 A1 | 3/2009 |
| EP | 1 876 906 B1 | 9/2009 |
| JP | 2002-220402 | 8/2002 |
| WO | WO-2005/120174 A2 | 12/2005 |
| WO | WO-2006/046943 A2 | 5/2006 |
| WO | WO-2006/095964 A1 | 9/2006 |
| WO | WO-2008/031092 A3 | 3/2008 |
| WO | WO-2008/060571 A2 | 5/2008 |
| WO | WO-2008/144583 A1 | 11/2008 |
| WO | WO-2009/082696 A1 | 7/2009 |
| WO | WO-2009/158658 A2 | 12/2009 |
| WO | WO-2010/036334 A1 | 4/2010 |
| WO | WO-2010/120939 A2 | 10/2010 |
| WO | WO-2010/123903 A1 | 10/2010 |
| WO | WO-2010/132414 A1 | 11/2010 |
| WO | WO-2010/138620 A1 | 12/2010 |
| WO | WO-2010/151606 A1 | 12/2010 |
| WO | WO-2011/027301 A1 | 3/2011 |
| WO | WO-2011/127157 | 10/2011 |
| WO | WO-2011/127160 | 10/2011 |
| WO | WO-2011/127161 | 10/2011 |
| WO | WO-2011/127165 | 10/2011 |
| WO | WO-2011/127167 | 10/2011 |
| WO | WO-2011/127169 | 10/2011 |
| WO | WO-2011/127171 | 10/2011 |
| WO | WO-2011/127172 | 10/2011 |

OTHER PUBLICATIONS

Bligh, E.G. et al., "A Rapid Method of Total Lipid Extraction and Purification," Canadian Journal of Biochemistry and Physiology, vol. 37, Aug. 1959, No. 8, pp. 911-917.

Borowitzka, M.A. "Commercial production of microalgae: ponds, tanks, tubes and ferments," Journal of Biotechnology 70 (1999), pp. 313-321.

Brennnan, L. et al., "Biofuels from microalgae—A review of technologies for production, processing, and extractions of biofuels and co-products," Renewable and Sustainable Energy Reviews 14 (2010), pp. 557-577.

Catchpole, O.J. et al. "The extraction and fractionation of specialty lipids using near critical fluids," J. of Supercritical Fluids 47 (2009), pp. 591-597.

Chisti, Y. "Biodiesel from microalgae," Biotechnology Advances 25 (2007), pp. 294-306.

Christie, W.W, Lipid Analysis, 3rd ed., Oily Press, Bridgewater, UK, 2003, pp. 97-102.

Communication Relating to the Results of the Partial International Search for corresponding International Patent Application No. PCT/US2011/031412 mailed Aug. 9, 2011, 4 pages.

International Search Report and Written Opinion for International Patent Application No. PCT/US2011/031404 mailed Aug. 3, 2011, 14 pages.

International Search Report and Written Opinion for International Patent Application No. PCT/US2011/031407 mailed Aug. 9, 2011, 12 pages.

International Search Report and Written Opinion for International Patent Application No. PCT/US2011/031408 mailed Aug. 9, 2011, 12 pages.

International Search Report and Written Opinion for International Patent Application No. PCT/US2011/031414 mailed Aug. 5, 2011, 13 pages.

International Search Report and Written Opinion for International Patent Application No. PCT/US2011/031417 mailed Aug. 3, 2011, 13 pages.

International Search Report and Written Opinion for International Patent Application No. PCT/US2011/031419 mailed Sep. 5, 2011, 15 pages.

International Search Report and Written Opinion for International Patent Application No. PCT/US2011/031421 mailed Aug. 3, 2011, 13 pages.

Daigger, G.T. et al., "Are Membrane Bioreactors Ready for Widespread Application?" Environmental Sciene & Technology, Oct. 1, 2005, pp. 399A-406A.

Database WPI, Week 200326, Thomson Scientific, London, GB; AN 2003-259841 & JP 2002 220402 A (Oriental Bio KK) Aug. 9, 2002, abstract, 2 pages.

de Morals Coutinho, C. et al., "State of art of the application of membrane technology to vegetable oils: A review," Food Research International 42 (2009), pp. 536-550.

Grima, E.M. et al., "Recovery of microalgal biomass and metabolites: process options and economics," Biotechnology Advances 20 (2003), pp. 491-515.

Harun, R. et al., "Bioprocess engineering of microlagae to produce a variety of consumer products," Renewable and Sustainable Energy Reviews 14 (2010), pp. 1037-1047.

Hejazi, M.A. et al., "Milking of microalgae," Trends in Biotechnology vol. 22, No. 4, Apr. 2004, pp. 189-194.

Herfindal, L. et al., "A high proportion of Baltic Sea benthic cynaobacterial isolates contain apoptogens able to induce rapid death of isolated rat hepatocytes," Toxicon 46 (2005), pp. 252-260.

Herrero, M. et al., "Sub- and supercritical fluid extraction of functional ingredients from different natural sources: Plants, food-by-products, algae and microalgae—A Review," Food Chemistry 98 (2006), pp. 136-148.

Huang, G. et al., "Biodiesel production by microalgal biotechnology," Applied Energy 87 (2010), pp. 38-46.

Huang, G. et al., "Rapid screening method for lipid production in alga based on Nile red fluorescence," Biomass and Bioenergy 33 (2009), pp. 1386-1392.

Ju Z.Y. et al., "Extraction, Denaturation and Hydrophobic Properties of Rice Flour Proteins," Journal of Food Science, vol. 66, No. 2, 2001, pp. 229-232.

Knuckey, R.M. et al., "Production of microalgal concentrates by flocculation and their assessment as aquaculture feeds," Aquaculural Engineering 35 (2006), pp. 300-313.

Koris, A. et al., "Dry degumming of vegetable oils by membrane filtration," Desalination 148 (2002), pp. 149-153.

Kumari, P. et al., "Tropical marine macroalgae as potential sources of nutritionally important PUFAs," Food Chemistry 120 (2010), pp. 749-757.

Lee, M. et al., "Isolation and Characterization of a Xanthophyll Aberrant Mutant of the Green Alga *Nannochloropsis oculata*," Marine Biotechnology, 2006, pp. 238-245.

Mata, Teresa M. et al., "Microalgae for biodiesel production and other applications: A review," Renewable and Sustainable Energy Reviews (2009), 16 pages.

Mercer, P. et al., "Developments in oil extraction from microalgae," Eur. J. Lipid Sci. Technol. 2011, 113, pp. 539-547.

Plaza, M. et al., "Screening for bioactive compounds from algae," Journal of Pharmaceuticals and Biomedical Analysis 51 (2010), pp. 450-455.

Ramirez, A. et al., "Lipid extraction from the microalga *Phaeodactylum tricornutum*," Eur. J. Lipid. Technol. 109 (2007), pp. 120-126.

Raynie, D.E., "Modem Extraction Techniques," Anal. Chem. 2006, 78, pp. 3997-4003.

Rhodes, C.J. "Oil from algae; salvation from peak oil?" Science Progress (2009), 92(1), pp. 39-90.

Rittmann, B.E. "Opportunities for Renewable Bioenergy Using Microorganisms," Biotechnology and Bioengineering, vol. 100, No. 2, Jun. 1, 2008, pp. 203-212.

Rossignol, N. et al., "Membrane technology for the continuous separation microalgae/culture medium: compared performances of cross-flow microfiltration and ultrafiltration," Aquacultutal Engineering 20 (1999), pp. 191-208.

Spolaore, P. et al. "Commercial Applications of Microalgae," Journal of Bioscience and Bioengineering, vol. 101, No. 2, pp. 87-96, 2006.

Steinitz, Y. et al., "A Mutant of the Cyanobacterium Plectonema Boryanum Resistant to Photooxidation," Plant Science Letters, vol. 16, Issues 2-3, pp. 327-335, Oct. 1979.

Uduman, N. et al. "Dewatering of microalgal cultures: A major bottleneck to algae-based fuels," Journal of Renewable and Sustainable Energy 2, 2010, pp. 012701-1-012701-15.

Voorhees, K.J. et al., "Analysis of Insoluble Carbonaceous Materials from Airborne Particles Collected in Pristine Region of Colorado," Journal of Analytical and Applied Pyrolysis, 18 (1991), pp. 189-205.

Wachowicz, M. et al. "The protein of the alga *Spirulina platensis*. (translated)." Database FSTA [Online] International Food Information Service (IFIS), Frankfurt-Main, DE; 1974, 1 page.

Webvitamins (2011, updated) "Globulin Protein Concentrate", www.webvitamins.com/Nutrient.aspx?id=2007, 1 page.

Wegmann, et al., "Short Communication: Effect of Temperature on Glycerol Retention in the Halotolerant Algae *Dunaliella* and *Asteromonas*," Plant Physiol., 1980, vol. 66, pp. 1196-1197.

"Seaweed Classification," Cornish Seaweed Resources, Seaweeds, Greens, Browns & Reds, 2011, 3 pages, retrieved from: http://www.cornishseaweedresources.org/redgreenbrown.htm, author unknown.

Environment Australia, "Setting National Fuel Quality Standards," Paper 6, National Standard for Biodiesel—Discussion Paper, Mar. 2003, downloaded from U.S. Appl. No. 11/979,699, No Author, pp. 1-103, 119 pages.

Gross et al., "The Nutritional Quality of *Scenedesmus acutus* in a Semi-Industrial Plant in Peru," J. Environ. Pathol. Toxicol. Oncol., May-Aug. 1986, Abstract Only, 1 page.

Lorenz, "A Technical Review of *Haematococcus* Algae," NatuRoseTM Technical Bulletin #060, Revision Date: Mar. 30, 1999, retrieved from the Internet: <http://www.cyanotech.com/pdfs/bioastin/axbul60.pdf>, retrieved on Dec. 14, 2011, 12 pages.

Rebolloso-Fuentes, et al., "Biomass Nutrient Profiles of the Microalga *Nannochloropsis*," J. Agric. Food Chem., 2001, vol. 49, No. 6, pp. 2966-2972.

Gibbs et al., "Natural Protoplast *Dunaliella* as a Source of Protein," Appl. Environ. Micribiol., Apr. 1976, Abstract Only, 1 page.

\* cited by examiner

Product 1: Proteins rich
Product 2: Polar Lipids rich
Product 3: Neutral lipids rich
Product 4: Residual biomass

METHODS OF AND SYSTEMS FOR ISOLATING CAROTENOIDS AND OMEGA-3 RICH OIL PRODUCTS FROM ALGAE

CROSS REFERENCE TO RELATED APPLICATIONS

This application is a continuation of U.S. Application Ser. No. 13/081,221, filed Apr. 6, 2011 now issued as U.S. Pat. No. 8,084,038, entitled Methods of and Systems for Isolating Nutraceutical Products from Algae which claims the benefit of U.S. Provisional Application No. 61/321,290, filed Apr. 6, 2010, entitled Extraction with Fractionation of Oil and Proteinaceous Material from Oleaginous Material and U.S. Provisional Application No. 61/321,286, filed Apr. 6, 2010, entitled Extraction With Fractionation of Oil and Co-Products from Oleaginous Material, the entire contents of which are hereby incorporated by reference herein.

FIELD OF THE INVENTION

The invention is concerned with extracting and fractionating algal products, including, but not limited to, oils and proteins. More specifically, the systems and methods described herein utilize step extraction and fractionation with a slightly nonpolar solvent to process wet algal biomass.

BACKGROUND OF THE INVENTION

Petroleum is a natural resource composed primarily of hydrocarbons. Extracting petroleum oil from the earth is expensive, dangerous, and often at the expense of the environment. Furthermore, world wide reservoirs of oil are dwindling rapidly. Costs also accumulate due to the transportation and processing required to convert petroleum oil into usable fuels such as gasoline and jet fuel.

Algae have gained a significant importance in recent years given their ability to produce lipids, which can be used to produce sustainable biofuel. This ability can be exploited to produce renewable fuels, reduce global climate change, and treat wastewater. Algae's superiority as a biofuel feedstock arises from a variety of factors, including high per-acre productivity compared to typical terrestrial oil crop plants, non-food based feedstock resources, use of otherwise non-productive, non-arable land, utilization of a wide variety of water sources (fresh, brackish, saline, and wastewater), production of both biofuels and valuable co-products such as carotenoids and chlorophyll.

Several thousand species of algae have been screened and studied for lipid production worldwide over the past several decades. Of these, about 300 species rich in lipid production have been identified. The lipid composition and content vary at different stages of the life cycle and are affected by environmental and culture conditions. The strategies and approaches for extraction are rather different depending on individual algal species/strains employed because of the considerable variability in biochemical composition and the physical properties of the algae cell wall. Conventional physical extraction processes, such as extrusion, do not work well with algae given the thickness of the cell wall and the small size (about 2 to about 20 nm) of algal cells. Furthermore, the large amounts of polar lipids in algal oil, as compared to the typical oil recovered from seeds, lead to refining issues.

Upon harvesting, typical algal concentrations in cultures range from about 0.1-1.0% (w/v). This means that as much as 1000 times the amount of water per unit weight of algae must be removed before attempting oil extraction. Currently, existing oil extraction methods for oleaginous materials strictly require almost completely dry feed to improve the yield and quality of the oil extracted. Due to the amount of energy required to heat the algal mass to dry it sufficiently, the algal feed to biofuel process is rendered uneconomical. Typically, the feed is extruded or flaked at high temperatures to enhance the extraction. These steps may not work with the existing equipment due to the single cell micrometric nature of algae. Furthermore, algal oil is very unstable due to the presence of double bonded long chain fatty acids. The high temperatures used in conventional extraction methods cause degradation of the oil, thereby increasing the costs of such methods.

It is known in the art to extract oil from dried algal mass by using hexane as a solvent. This process is energy intensive. The use of heat to dry and hexane to extract produces product of lower quality as this type of processing causes lipid and protein degradation.

Algal oil extraction can be classified into two types: disruptive or non-disruptive methods.

Disruptive methods involve cell lies by mechanical, thermal, enzymatic or chemical methods. Most disruptive methods result in emulsions, requiring an expensive cleanup process. Algal oils contain a large percentage of polar lipids and proteins which enhance the emulsification of the neutral lipids. The emulsification is further stabilized by the nutrient and salt components left in the solution. The emulsion is a complex mixture, containing neutral lipids, polar lipids, proteins, and other algal products, which extensive refining processes to isolate the neutral lipids, which are the feed that is converted into biofuel.

Non-disruptive methods provide low yields. Milking is the use of solvents or chemicals to extract lipids from a growing algal culture. While sometimes used to extract algal products, milking may not work with some species of algae due to solvent toxicity and cell wall disruption. This complication makes the development of a generic process difficult. Furthermore, the volumes of solvents required would be astronomical due to the maximum attainable concentration of the solvent in the medium.

Multiphase extractions would require extensive distillations, using complex solvent mixtures, and necessitating mechanisms for solvent recovery and recycle. This makes such extractions impractical and uneconomical for use in algal oil technologies.

Accordingly, to overcome these deficiencies, there is a need in the art for improved methods and systems for extraction and fractionating algal products, in particular algal oil, algal proteins, and algal carotenoids.

BRIEF SUMMARY OF THE INVENTION

Embodiments described herein relate generally to systems and methods for extracting lipids of varying polarities from an oleaginous material, including for example, an algal biomass. In particular, embodiments described herein concern extracting lipids of varying polarities from an algal biomass using solvents of varying polarity and/or a series of membrane filters. In some embodiments, the filter is a microfilter.

In some embodiments of the invention, a single solvent and water are used to extract and fractionate components present in an oleaginous material. In other embodiments, these components include, but are not limited to, proteins, polar lipids, and neutral lipids. In still other embodiments, more than one solvent is used. In still other embodiments, a mixture of solvents is used.

In some embodiments, the methods and systems described herein are useful for extracting coproducts of lipids from oleaginous material. Examples of such coproducts include, without limitation, proteinaceous material, chlorophyll, and carotenoids. Embodiments of the present invention allow for the simultaneous extraction and fractionation of algal products from algal biomass in a manner that allows for the production of both fuels and nutritional products.

In another embodiment of the invention, a method of isolating nutraceuticals products from algae is provided.

In a further embodiment of the invention, a method of isolating carotenoids and omega-3 rich oil from algae includes dewatering substantially intact algal cells to make an algal biomass and adding a first ethanol fraction to the algal biomass in a ratio of about 1 part ethanol to about 1 part algal biomass by weight. The method also includes separating a first substantially solid biomass fraction from a first substantially liquid fraction comprising proteins and combining the first substantially solid biomass fraction with a second ethanol fraction in a ratio of about 1 part ethanol to about 1 part solids by weight. The method further includes separating a second substantially solid biomass fraction from a second substantially liquid fraction comprising polar lipids and combining the second substantially solid biomass fraction with a third ethanol solvent fraction in a ratio of about 1 part ethanol to about 1 part substantially solid biomass by weight. The method also includes separating a third substantially solid biomass fraction from a third substantially liquid fraction comprising neutral lipids, wherein the third substantially solid biomass fraction comprises carbohydrates and separating the neutral lipids into carotenoids and omega-3 rich oil.

In yet another embodiment of the invention, the method also includes isolating carotenoids, omega-3 rich oil, carbohydrates and polar lipids; isolating the polar lipids from components that are not polar lipid components; and/or isolating carotenoids from non-carotenoid components.

In still a further embodiment of the invention, the method also includes processing the polar lipids into at least one of lubricants, detergents, and food additives.

In another embodiment of the invention, at least one of the first, second, and third solvent sets comprises an alcohol. Optionally, the alcohol is ethanol.

DETAILED DESCRIPTION

Definitions

Figure 1A:
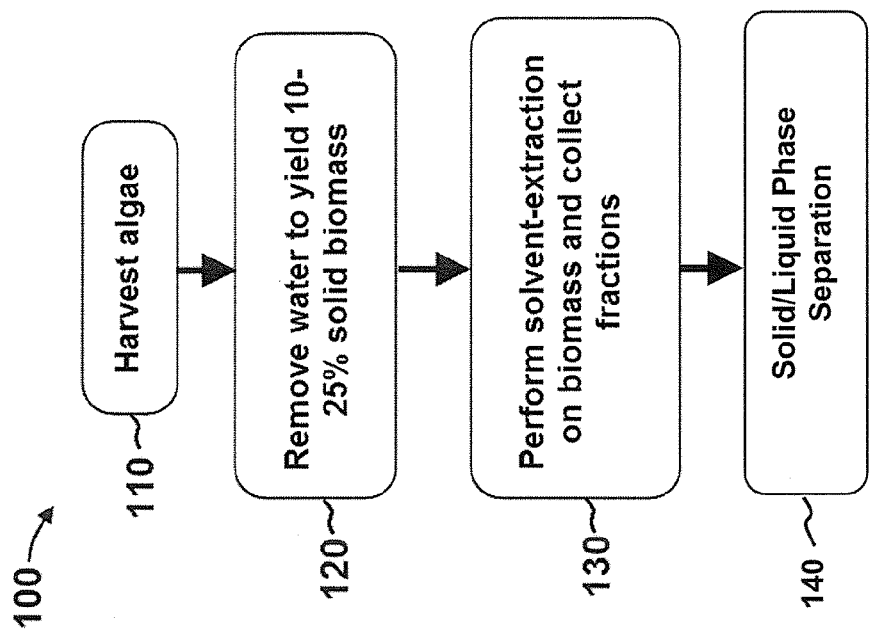
FIG. 1A is a flowchart of steps involved in a method according to an exemplary embodiment of the present disclosure.

The term "conduit" or any variation thereof, as used herein, includes any structure through which a fluid may be conveyed. Non-limiting examples of conduit include pipes, tubing, channels, or other enclosed structures.

The term "reservoir" or any variation thereof, as used herein, includes any body structure capable of retaining fluid. Non-limiting examples of reservoirs include ponds, tanks, lakes, tubs, or other similar structures.

The term "about" or "approximately," as used herein, are defined as being close to as understood by one of ordinary skill in the art, and in one non-limiting embodiment the terms are defined to be within 10%, preferably within 5%, more preferably within 1%, and most preferably within 0.5%.

The terms "inhibiting" or "reducing" or any variation of these terms, as used herein, includes any measurable decrease or complete inhibition to achieve a desired result.

The term "effective," as used herein, means adequate to accomplish a desired, expected, or intended result.

The use of the word "a" or "an" when used in conjunction with the term "comprising" herein may mean "one," but it is also consistent with the meaning of "one or more," "at least one," and "one or more than one."

The term "or" as used herein, means "and/or" unless explicitly indicated to refer to alternatives only or the alternatives are mutually exclusive, although the disclosure supports a definition that refers to only alternatives and "and/or."

The use of the term "wet" as used herein, is used to mean containing about 50% to about 99.9% water content. Water content may be located either intracellularly or extracellularly.

The use of the term "solvent set" as used herein, is used to mean composition comprising one or more solvents. These solvents can be amphipatic (also known as amphiphilic or slightly nonpolar), hydrophilic, or hydrophobic. In some embodiment, these solvents are water miscible and in others, they are immiscible in water. Non-limiting example of solvents that may be used to practice the methods of the instant invention include methanol, ethanol, isopropanol, acetone, ethyl acetate, and acetonitrile, alkanes (hexane, pentane, heptane, octane), esters (ethyl acetate, butyl acetate), ketones (methyl ethyl ketone (MEK), methyl isobutyl ketone (MIBK)), aromatics (toluene, benzene, cyclohexane, tetrahydrofuran), haloalkanes (chloroform, trichloroethylene), ethers (diethyl ether), and mixtures (diesel, jet fuel, gasoline).

The term "oil" as used herein includes compositions containing neutral lipids and polar lipids. The terms "algae oil" and "algal oil" as used herein are used interchangeably.

The term "diffusate" or "permeate" as used herein may refer to material that has passed through a separation device, including, but not limited to a filter or membrane.

The term "retentate" as used herein may refer to material that remains after the diffusate has passed through a separation device.

As used herein, the words "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or method steps.

The term "polar lipids" or any variation thereof, as used herein, includes, but is not limited to, phospholipids and glycolipids.

The term "neutral lipids" or any variation thereof, as used herein, includes, but is not limited to, triglycerides, diglycerides, monoglycerides, carotenoids, waxes, sterols.

The term "solid phase" as used herein refers to a collection of material that is generally more solid than not, and is not intended to mean that all of the material in the phase is solid. Thus, a phase having a substantial amount of solids, while retaining some liquids, is encompassed within the meaning of that term. Meanwhile, the term "liquid phase", as used herein, refers to a collection of material that is generally more liquid than not, and such collection may include solid materials.

The term "biodiesel" as used herein refers to methyl or ethyl esters of fatty acids derived from algae The term "nutraceutical" as used herein refers to a food product that provides health and/or medical benefits. Non-limiting examples include carotenoids, carotenes, xanthophylls such as zeaxanthin, astaxanthin, and lutein.

The term "biofuel" as used herein refers to fuel derived from biological source. Non-limiting examples include biodiesel, jet fuel, diesel, jet fuel blend stock and diesel blend stock.

The term "impurities", when used in connection with polar lipids, as used herein, refers to all components other than the products of interest that are coextracted or have the same properties as the product of interest.

The term "lubricants", when used in connection with polar lipids, as used herein refers to hydrotreated algal lipids such as C16-C20 alkanes.

The term "detergents", when used in connection with polar lipids, as used herein refers to glycolipids, phospholipids and derivatives thereof.

The term "food additives", when used in connection with polar lipids, as used herein refers to soy lecithin substitutes or phospholipids derived from algae.

The term "non-glycerin matter" as used herein refers to any impurity that separates with the glycerin fraction. A further clean up step will remove most of what is present in order to produce pharmaceutical grade glycerin.

The term "unsaturated fatty acids" as used herein refers to fatty acids with at least one double carbon bond. Non-limiting examples of unsaturated fatty acids include palmitoleic acid, margaric acid, stearic acid, oleic acid, octadecenoic acid, linoleic acid, gamma-linoleic acid, alpha linoleic acid, arachidic acid, eicosenoic acid, homogamma linoleic acid, arachidonic acid, eicosapenenoic acid, behenic, docosadienoic acid, heneicosapentaenoic, docosatetraenoic acid. Fatty acids having 20 or more carbon atoms in the backbone are generally referred to as "long chain fatty acids". The fatty acids having 19 or fewer carbon atoms in the backbone are generally referred to as "short chain fatty acids".

Unsaturated long chain fatty acids include, but are not limited to, omega-3 fatty acids, omega-6 fatty acids, and omega-9 fatty acids. The term "omega-3 fatty acids" as used herein refers to, but is not limited to the fatty acids listed in Table 1.

TABLE 1

| Common name | Lipid name | Chemical name |
| --- | --- | --- |
| Eicosatrienoic acid (ETE) | 20:3 (n-3) | all-cis-11,14,17-eicosatrienoic acid |
| Eicosatetraenoic acid (ETA) | 20:4 (n-3) | all-cis-8,11,14,17-eicosatetraenoic acid |
| Eicosapentaenoic acid (EPA) | 20:5 (n-3) | all-cis-5,8,11,14,17-eicosapentaenoic acid |
| Heneicosapentaenoic acid (HPA) | 21:5 (n-3) | all-cis-6,9,12,15,18-heneicosapentaenoic acid |
| Docosapentaenoic acid (DPA), | 22:5 (n-3) | all-cis-7,10,13,16,19-docosapentaenoic acid |
| Clupanodonic acid | 22:6 (n-3) | all-cis-4,7,10,13,16,19-docosahexaenoic acid |
| Docosahexaenoic acid (DHA) | 24:5 (n-3) | all-cis-9,12,15,18,21-tetracosapentaenoic acid |
| Tetracosapentaenoic acid | 24:6 (n-3) | all-cis-6,9,12,15,18,21-tetracosahexaenoic acid |

The term "jet fuel blend stock" as used herein refers to alkanes with the carbon chain lengths appropriate for use as jet fuels.

The term "diesel blend stock" as used herein refers to alkanes with the carbon chain lengths appropriate for use as diesel.

The term "animal feed" as used herein refers to algae-derived substances that can be consumed and used to provide nutritional support for an animal.

The term "human food" as used herein refers to algae-derived substances that can be consumed to provide nutritional support for people. Algae-derived human food products can contain essential nutrients, such as carbohydrates, fats, proteins, vitamins, or minerals.

The term "bioremediation" as used herein refers to use of algal growth to remove pollutants, such as, but not limited to, nitrates, phosphates, and heavy metals, from industrial wastewater or municipal wastewater.

The term "wastewater" as used herein refers to industrial wastewater or municipal wastewater that contain a variety of contaminants or pollutants, including, but not limited to nitrates, phosphates, and heavy metals.

The term "enriched", as used herein, shall mean about 50% or greater content.

The term "substantially", as used herein, shall mean mostly.

The term "globulin proteins" as used herein refers to salt soluble proteins.

The term "albumin proteins" as used herein refers to water soluble proteins.

The term "glutelin proteins" as used herein refers to alkali soluble proteins.

The term "prolamin proteins" as used herein refers to alcohol soluble proteins. Non-limiting examples of prolamin proteins are gliadin, zein, hordein, avenin.

The term "algal culture" as used herein refers to algal cells in culture medium.

The term "algal biomass" as used herein refers to an at least partially dewatered algal culture.

The term "dewatered" as used herein refers to the removal of at least some water.

The term "algal paste" as used herein refers to a partially dewatered algal culture having fluid properties that allow it to flow. Generally an algal paste has a water content of about 90%.

The term "algal cake" as used herein refers to a partially dewatered algal culture that lacks the fluid properties of an algal paste and tends to clump. Generally an algal cake has a water content of about 60% or less.

Saltwater algal cells include, but are not limited to, marine and brackish algal species. Saltwater algal cells are found in nature in bodies of water such as, but not limited to, seas, oceans, and estuaries. Non-limiting examples of saltwater algal species include *Nannochloropsis* sp., *Dunaliella* sp.

Freshwater algal cells are found in nature in bodies of water such as, but not limited to, lakes and ponds. Non-limiting examples of freshwater algal species include *Scendescemus* sp., *Haemotococcus* sp.

Non-limiting examples of microalgae that can be used with the methods of the invention are members of one of the following divisions: Chlorophyta, Cyanophyta (Cyanobacteria), and Heterokontophyta. In certain embodiments, the microalgae used with the methods of the invention are members of one of the following classes: Bacillariophyceae, Eustigmatophyceae, and Chrysophyceae. In certain embodiments, the microalgae used with the methods of the invention are members of one of the following genera: *Nannochloropsis, Chlorella, Dunaliella, Scenedesmus, Selenastrum, Oscillatoria, Phormidium, Spirulina, Amphora*, and *Ochromonas*.

Non-limiting examples of microalgae species that can be used with the methods of the present invention include: *Achnanthes orientalis, Agmenellum* spp., *Amphiprora hyaline, Amphora coffeiformis, Amphora coffeiformis* var. *linea, Amphora coffeiformis* var. *punctata, Amphora coffeiformis* var. *taylori, Amphora coffeiformis* var. *tenuis, Amphora delicatissima, Amphora delicatissima* var. *capitata, Amphora* sp., *Anabaena, Ankistrodesmus, Ankistrodesmus falcatus, Boekelovia hooglandii, Borodinella* sp., *Botryococcus braunii, Botryococcus sudeticus, Bracteococcus minor, Bracteococcus medionucleatus, Carteria, Chaetoceros gracilis, Chaetoceros muelleri, Chaetoceros muelleri* var. *subsalsum, Chaetoceros* sp., *Chlamydomas perigranulata, Chlorella anitrata, Chlorella antarctica, Chlorella aureoviridis, Chlorella Candida, Chlorella capsulate, Chlorella desiccate, Chlorella ellipsoidea, Chlorella emersonii, Chlorella fusca, Chlorella fusca* var. *vacuolate, Chlorella glucotropha, Chlorella infusionum, Chlorella infusionum* var. *actophila, Chlorella infusionum* var. *auxenophila, Chlorella kessleri, Chlorella lobophora, Chlorella luteoviridis, Chlorella luteoviridis* var. *aureoviridis, Chlorella luteoviridis* var. *lutescens, Chlorella miniata, Chlorella minutissima, Chlorella mutabilis, Chlorella nocturna, Chlorella ovalis, Chlorella parva, Chlorella photophila, Chlorella pringsheimii, Chlorella protothecoides, Chlorella protothecoides* var. *acidicola, Chlorella regularis, Chlorella regularis* var. *minima, Chlorella regularis* var. *umbricata, Chlorella reisiglii, Chlorella saccharophila, Chlorella saccharophila* var. *ellipsoidea, Chlorella salina, Chlorella simplex, Chlorella sorokiniana, Chlorella* sp., *Chlorella sphaerica, Chlorella stigmatophora, Chlorella vanniellii, Chlorella vulgaris, Chlorella vulgaris* fo. *tertia, Chlorella vulgaris* var. *autotrophica, Chlorella vulgaris* var. *viridis, Chlorella vulgaris* var. *vulgaris, Chlorella vulgaris* var. *vulgaris* fo. *tertia, Chlorella vulgaris* var. *vulgaris* fo. *viridis, Chlorella xanthella, Chlorella zofingiensis, Chlorella trebouxioides, Chlorella vulgaris, Chlorococcum infusionum, Chlorococcum* sp., *Chlorogonium, Chroomonas* sp., *Chrysosphaera* sp., *Cricosphaera* sp., *Crypthecodinium cohnii, Cryptomonas* sp., *Cyclotella cryptica, Cyclotella meneghiniana, Cyclotella* sp., *Dunaliella* sp., *Dunaliella bardawil, Dunaliella bioculata, Dunaliella granulate, Dunaliella maritime, Dunaliella minuta, Dunaliella parva, Dunaliella peircei, Dunaliella primolecta, Dunaliella salina, Dunaliella terricola, Dunaliella tertiolecta, Dunaliella viridis, Dunaliella tertiolecta, Eremosphaera viridis, Eremosphaera* sp., *Ellipsoidon* sp., *Euglena* spp., *Franceia* sp., *Fragilaria crotonensis, Fragilaria* sp., *Gleocapsa* sp., *Gloeothamnion* sp., *Haematococcus pluvialis, Hymenomonas* sp., *Isochrysis* aff. *galbana, Isochrysis galbana, Lepocinclis, Micractinium, Micractinium, Monoraphidium minutum, Monoraphidium* sp., *Nannochloris* sp., *Nannochloropsis salina, Nannochloropsis* sp., *Navicula acceptata, Navicula biskanterae, Navicula pseudotenelloides, Navicula pelliculosa, Navicula saprophila, Navicula* sp., *Nephrochloris* sp., *Nephroselmis* sp., *Nitschia communis, Nitzschia alexandrine, Nitzschia closterium, Nitzschia communis, Nitzschia dissipata, Nitzschia frustulum, Nitzschia hantzschiana, Nitzschia inconspicua, Nitzschia intermedia, Nitzschia microcephala, Nitzschia pusilla, Nitzschia pusilla elliptica, Nitzschia pusilla monoensis, Nitzschia quadrangular, Nitzschia* sp., *Ochromonas* sp., *Oocystis parva, Oocystis pusilla, Oocystis* sp., *Oscillatoria limnetica, Oscillatoria* sp., *Oscillatoria subbrevis, Parachlorella kessleri, Pascheria acidophila, Pavlova* sp., *Phaeodactylum tricomutum, Phagus, Phormidium, Platymonas* sp., *Pleurochrysis camerae, Pleurochrysis dentate, Pleurochrysis* sp., *Prototheca wickerhamii, Prototheca stagnora, Prototheca portoricensis, Prototheca moriformis, Prototheca zopfii, Pseudochlorella aquatica, Pyramimonas* sp., *Pyrobotrys, Rhodococcus opacus, Sarcinoid chrysophyte, Scenedesmus armatus, Schizochytrium, Spirogyra, Spirulina platensis, Stichococcus* sp., *Synechococcus* sp., *Synechocys-*

*tisf, Tagetes erecta, Tagetes patula, Tetraedron, Tetraselmis* sp., *Tetraselmis suecica, Thalassiosira weissflogii*, and *Viridiella fridericiana*.

In other embodiments, the biomass can be plant material, including but not limited to soy, corn, palm, camelina, jatropha, canola, coconut, peanut, safflower, cottonseed, linseed, sunflower, rice bran, and olive.

Systems and methods for extracting lipids and coproducts (e.g., proteins) of varying polarity from a wet oleaginous material, including for example, an algal biomass, are disclosed. In particular, the methods and systems described herein concern the ability to both extract and fractionate the algae components by doing sequential extractions with a hydrophilic solvent/water mixture that becomes progressively less polar (i.e., water in solvent/water ratio is progressively reduced as one proceed from one extraction step to the next). In other words, the interstitial solvent in the algae (75% of its weight) is initially water and is replaced by the slightly nonpolar solvent gradually to the azeotrope of the organic solvent. This results in the extraction of components soluble at the polarity developed at each step, thereby leading to simultaneous fractionation of the extracted components. Extraction of proteinaceous byproducts by acid leaching and/or alkaline extraction is also disclosed.

In some embodiments of the invention, a single solvent and water are used to extract and fractionate components present in an oleaginous material. In other embodiments, a solvent set and water are used to extract and fractionate components present in an oleaginous material. In some embodiments the oleaginous material is wet. In other embodiments, the oleaginous material is algae.

Polar lipid recovery depends mainly on its ionic charge, water solubility, and location (intracellular, extracellular or membrane bound). Examples of polar lipids include, but are not limited to, phospholipids and glycolipids. Strategies that can be used to separate and purify polar lipids can roughly be divided into batch or continuous modes. Examples of batch modes include precipitation (pH, organic solvent), solvent extraction and crystallization. Examples of continuous modes include centrifuging, adsorption, foam separation and precipitation, and membrane technologies (tangential flow filtration, diafiltration and precipitation, ultra filtration).

Other objects, features and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

Surprisingly, the proposed non-disruptive extraction process results in over 90% recovery. The small amount of polar lipids in the remaining biomass enhances its value when the remaining biomass is used for feed. This is due, at least in part, to the high long chain unsaturated fatty acid content of the biomass. In addition, ethanol extracts can further be directly transesterified. Furthermore, unlike the existing conventional methods, the methods and systems described herein are generic for any algae, and enable recovery of a significant portion of the valuable components, including polar lipids, in the algae by the use of a water miscible organic solvent gradient.

The neutral lipid fraction obtained by the use of the present invention possesses a low metal content, thereby enhancing stability of the lipid fraction, and reducing subsequent processing steps. Metals tend to make neutral lipids unstable due to their ability to catalyze oxidation. Furthermore, metals inhibit hydrotreating catalysts, necessitating their removal before a neutral lipid mixture can be refined. The systems and methods disclosed herein allow for the extraction of metals in the protein and/or the polar lipid fractions. This is advantageous because proteins and polar lipids are not highly affected by metal exposure, and in some cases are actually stabilized by metals.

The systems and methods disclosed herein can start with wet biomass, reducing the drying and dewatering costs. Compared to conventional extraction processes, the disclosed extraction and fractionation processes should have relatively low operating costs due to the moderate temperature and pressure conditions, along with the solvent recycle. Furthermore, conventional extraction processes are cost prohibitive and cannot meet the demand of the market.

Another aspect of the systems and methods described herein is the ability to accomplish preliminary refining, which is the separation of polar lipids from neutral lipids during the extraction process. The differences between algal oil used in exemplary embodiments and vegetable oils used in previous embodiments include the percentage of individual classes of lipids. An exemplary algal crude oil composition is compared with vegetable oil shown in Table 2 below:

TABLE 2

|  | Algal Crude Oil (w/w) | Vegetable Oil (w/w) |
| --- | --- | --- |
| Neutral lipids | 30-90% | 90-98% |
| Phospholipids | 10-40% | 1-2% |
| Glycolipids | 10-40% | <1% |
| Free fatty acids | 1-10% | <3% |
| Waxes | 2-5% | <2% |
| Pigments | 1-4% | Ppm |

Degumming (physical and/or chemical) of vegetable oil is done in order to remove polar lipids (e.g., glycolipids and phospholipids). Vegetable oil that has been chemically degummed retains a significant quantity of neutral lipid. This neutral lipid fraction is further removed from the degummed material using solvent extraction or supercritical/subcritical fluid extraction or membrane technology. In contrast, separation of the neutral lipids from an oleaginous algal biomass is far more difficult than from a vegetable oil feedstock due to the presence of large quantities of polar lipids typically found in algal oil (see Table 2). This is because the larger percentage of polar lipids present in algal oil enhances the emulsification of the neutral lipids. The emulsification is further stabilized by the nutrient and salt components left in the solution. The presence of polar lipids, along with metals, results in processing difficulties for separation and utilization of neutral lipids. However, because polar lipids have an existing market, their recovery would add significant value to the use of algal oil to generate fuels.

Polar lipids are surfactants by nature due to their molecular structure and have a huge existing market. Many of the existing technologies for producing polar lipids are raw material or cost prohibitive. Alternative feedstocks for glycolipids and phospholipids are mainly algae oil, oat oil, wheat germ oil and vegetable oil. Algae oil typically contains about 30-5% (w/w) polar lipids depending on the species, physiological status of the cell, culture conditions, time of harvest, and the solvent utilized for extraction. Further, the glycerol backbone of each polar lipid has two fatty acid groups attached instead of three in the neutral lipid triacylglycerol. Transesterification of polar lipids may yield only two-thirds of the end product, i.e., esterified fatty acids, as compared to that of neutral lipids, on a per mass basis. Hence, removal and recovery of the polar lipids would not only be highly beneficial in producing high quality biofuels or triglycerides from algae, but also generate value-added co-products glycolipids and phospholipids, which in turn can offset the cost associated with algae-based biofuel production. The ability to easily recover and fractionate the various oil and co-products produced by algae is advantageous to the economic success of the algae oil process.

A further aspect of the methods and systems described herein is the ability to extract proteins from an oleaginous material, such as algal biomass. The methods disclosed herein of extraction of proteinaceous material from algal biomass comprise a flexible and highly customizable process of extraction and fractionation. For example, in some embodiments, extraction and fractionation occur in a single step, thereby providing a highly efficient process. Proteins sourced from such biomass are useful for animal feeds, food ingredients and industrial products. For example, such proteins are useful in applications such as fibers, adhesives, coatings, ceramics, inks, cosmetics, textiles, chewing gum, and biodegradable plastics.

Another aspect of the methods and systems described herein involves varying the ratio of algal biomass to solvent based on the components to be extracted. In one embodiment, an algal biomass is mixed with an equal weight of solvent. In another embodiment, an algal biomass is mixed with a lesser weight of solvent. In yet another embodiment, an algal biomass is mixed with a greater weight of solvent. In some embodiments, the amount of solvent mixed with an algal biomass is calculated based on the solvent to be used and the desired polarity of the algal biomass/solvent mixture. In still other embodiments, the algal mass is extracted in several steps. In an exemplary embodiment, an algal biomass is sequentially extracted, first with about 50-60% of its weight with a slightly nonpolar, water miscible solvent. Second, the remaining algal solids are extracted using about 70% of the solids' weight in solvent. A third extraction is then performed using about 90% of the solid's weight in solvent. Having been informed of these aspects of the invention, one of skill in the art would be able to use different solvents of different polarities by adjusting the ratios of algal biomass and/or solid residuals to the desired polarity in order to selectively extract algal products.

For example, in preferred embodiment, the solvent used is ethanol. Components may be selectively isolated by varying the ratio of solvent. Proteins can be extracted from an algal biomass with about 50% ethanol, polar lipids with about 80% ethanol, and neutral lipids with about 95% or greater ethanol. If methanol were to be used, the solvent concentration to extract proteins from an algal biomass would be about 70%. Polar lipids would require about 90% methanol, and neutral lipids would require about 100% methanol.

Embodiments of the systems and methods described herein exhibit surprising and unexpected results. First of all, the recovery/extraction process can be done on a wet biomass. This is a major economic advantage as exemplary embodiments avoid the use of large amounts of energy required to dry and disrupt the cells. Extraction of neutral lipids from a dry algal biomass is far more effective using the systems and methods of the present invention. The yields obtained from the disclosed processes are significantly higher and purer than those obtained by conventional extractions. This is because conventional extraction frequently results in emulsions, rendering component separations extremely difficult.

Exemplary embodiments may be applied to any algae or non-algae oleaginous material. Exemplary embodiments may use any water-miscible slightly nonpolar solvent, including, but not limited to, methanol, ethanol, isopropanol, acetone, ethyl acetate, and acetonitrile. Specific embodiments may use a green renewable solvent, such as ethanol. The alcohol solvents tested resulted in higher yield and purity of isolated neutral lipids. Ethanol is relatively economical to purchase as compared to other solvents disclosed herein. In some exemplary embodiments, extraction and fractionation can be performed in one step followed by membrane-based purification if needed. The resulting biomass is almost devoid of water and can be completely dried with lesser energy than an aqueous algae slurry.

In some exemplary embodiments, the solvent used to extract is ethanol. Other embodiments include, but are not limited to, cyclohexane, petroleum ether, pentane, hexane, heptane, diethyl ether, toluene, ethyl acetate, chloroform, dicholoromethane, acetone, acetonitrile, isopropanol, and methanol. In some embodiments, the same solvent is used in sequential extraction steps. In other embodiments, different solvents are used in each extraction step. In still other embodiments, two or more solvents are mixed and used in one or more extraction steps.

In some embodiments of the methods described herein, a mixture of two or more solvents used in any of the extraction steps includes at least one hydrophilic solvent and at least one hydrophobic solvent. When using such a mixture, the hydrophilic solvent extracts the material from the biomass via diffusion. Meanwhile, a relatively small amount of hydrophobic solvent is used in combination and is involved in a liquid-liquid separation such that the material of interest is concentrated in the small amount of hydrophobic solvent. The two different solvents then form a two-layer system, which can be separated using techniques known in the art. In such an implementation, the hydrophobic solvent can be any one or more of an alkane, an ester, a ketone, an aromatic, a haloalkane, an ether, or a commercial mixture (e.g., diesel, jet fuel, gasoline).

In some embodiments, the extraction processes described herein incorporate pH excursion in one or more steps. Such pH excursion is useful for isolating proteinaceous material. In some embodiments, the pH of the extraction process is acid (e.g., less than about 5). In some embodiments, the pH of the extraction process is alkaline (e.g., greater than about 10).

The use of hexane in conventional extraction procedures contaminates algal biomass such that coproducts may not be used in food products. Embodiments of the present invention are superior to those known in the art as they require the use of far less energy and render products suitable for use as fuels as well as foodstuffs and nutrient supplements.

It is contemplated that any embodiment discussed in this specification can be implemented with respect to any method or system of the invention, and vice versa. Furthermore, systems of the invention can be used to achieve methods of the invention.

DESCRIPTION OF EXEMPLARY EMBODIMENTS

For solvent extraction of oil from algae the best case scenario is a solvent which selectively extracts triacylglycerols (TAG) and leaving all polar lipids and non-TAG neutral lipids such as waxes, sterols in the algal cell with high recoveries. The second option would be selectively extract polar lipids and then extract purer neutral lipids devoid of polar lipids, resulting in high recovery. The last option would be to extract all the lipids and achieve very high recovery in one or two steps.

Referring now to FIG. 1A, a flowchart 100 provides an overview of the steps involved in exemplary embodiments of methods used in the fractionation and purification of lipids from an algae-containing biomass. In a first step 110, algal cells are harvested. In a subsequent step 120, water is removed from algal cells to yield a 10-25% solid biomass. In step 130, a solvent-based extraction is performed on the biomass and the fractions are collected. In some embodiments, step 130 will also incorporate pH-based extraction and fraction collection. Finally, a solid/liquid phase separation, including, but not limited to techniques such as filtration, decanting, and centrifugation, may be performed in a step 140 to in order to separate out smaller lipid components.

The algae biomass when harvested in step 110 typically consists of about 1-5 g/L of total solids. The biomass can be partially dewatered in step 120 using techniques including, but not limited to, dissolved air floatation, membrane filtration, flocculation, sedimentation, filter pressing, decantation or centrifugation. Dewatering is the removal of some, most, or all of the water from a solid or semisolid substance. Embodiments of the present invention utilize dewatering techniques to remove water from a harvested algal biomass. Dewatering can be carried out using any one of or a combination of any of the methods described herein, as well as by any other methods known to one of skill in the art.

The dewatered algae biomass resulting from step 120 typically consists of about 10-30% solids. This biomass can then be extracted with water miscible slightly nonpolar solvents (e.g., alcohols), in a multistage countercurrent solvent extraction process segregating the fractions at each stage. This type of process can reduce both capital and operating expenses. In some embodiments, the biomass also undergoes acid and/or alkaline extraction to fractionate protein material.

In some embodiments, dewatering of an algal biomass can be carried out by treating the harvested algal biomass with a solvent such as ethanol. The algal biomass is then allowed to settle out of solution and the liquids may then be removed by methods such as, but not limited to, siphoning. This novel method of dewatering has lower capital and operating costs than known methods, enables solvent recycling, reduces the cost of drying the biomass, and has the added benefit of decreasing the polarity of the algal biomass prior to beginning extraction and/or separation of algal components. In fact, it is theorized that the solvent-based sedimentation processes described herein are effective, in part, due to the fact that organic solvents reduce or neutralize the negative charge on the algae surface. In some embodiments of the invention, dewatering methods are combined in order to remove even more water. In some embodiments, the addition of solvent during the dewatering process begins the process of extraction.

Figure 1B:
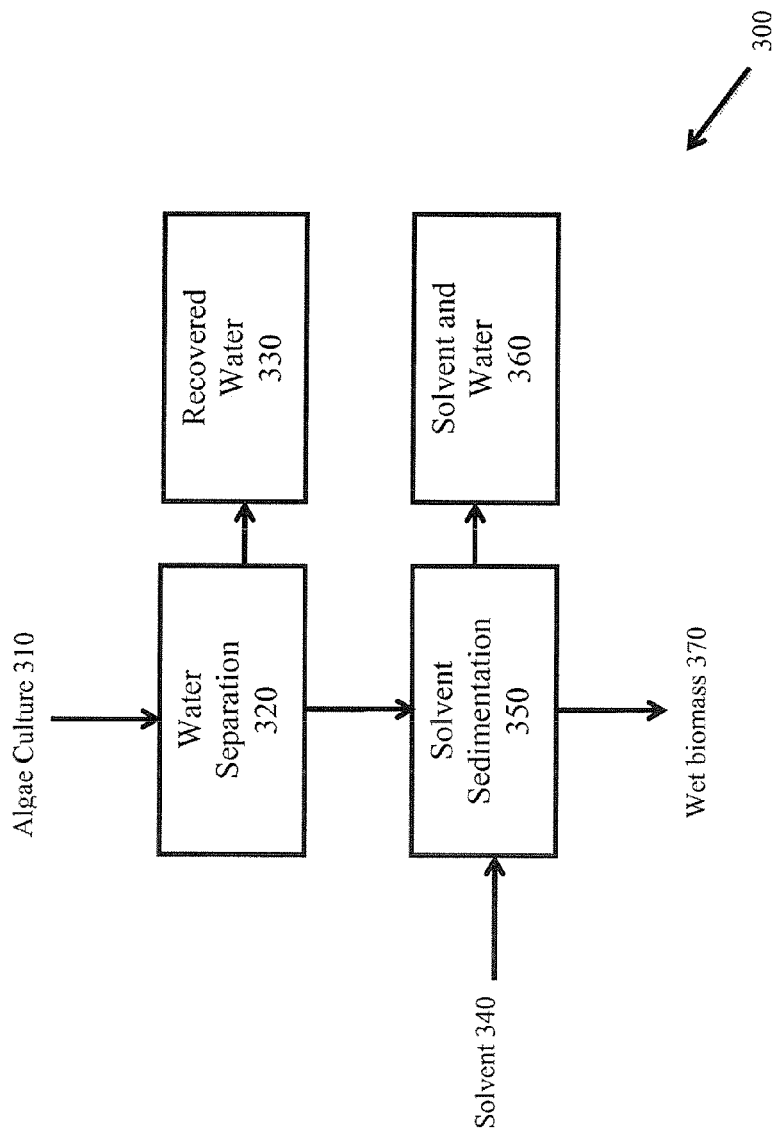
FIG. 1B is a schematic diagram of an exemplary embodiment of a dewatering process according to the present disclosure.

FIG. 1B shows an illustrative implementation of a dewatering process 300. An algal culture 310 having a final dry weight of about 1 g/L to about 10 g/L (i.e., 0.1-1% w/w) is subjected to a water separation process 320. Process 320 can include centrifugation, decanting, settling, or filtration. In one embodiment, a sintered metal tube filter is used to separate the algal biomass from the water of the culture. When using such a filter, the recovered water 330 is recycled directed to other algae cultures. Meanwhile, the algal biomass recovered has been concentrated to an "algae paste" with a algae density as high as about 200 g/L (i.e., 10-20% w/w). This concentrated algae paste is then treated with a solvent 340 in a solvent-based sedimentation process 350.

Sedimentation process 350 involves adding solvent 340 to the algae paste to achieve a mixture having a weight/weight solvent to biomass ratio of between about 1:1 to about 1:10. The algae is allowed to settle in a settling vessel, and a solvent/water mixture 360 is removed by, for example, siphoning and/or decanting. The solvent can be recovered and reused by well-known techniques, such as distillation and/or pervaporation. The remaining wet biomass 370 is expected to have a solids content of about 30% to about 60% w/w in an alcohol and water solution.

Solvents ideal for dewatering are industrially common water-soluble solvents with densities over 1.1 g/mL or below 0.9 g/mL. Examples include isopropanol, acetone, acetonitrile, t-butyl alcohol, ethanol, methanol, 1-propanol, heavy water ($D_2O$), ethylene glycol, and/or glycerin. If the solvent density is over 1.1 g/mL then the algae biomass would float rather than create a sediment at the bottom of the settling vessel.

Figure 2:
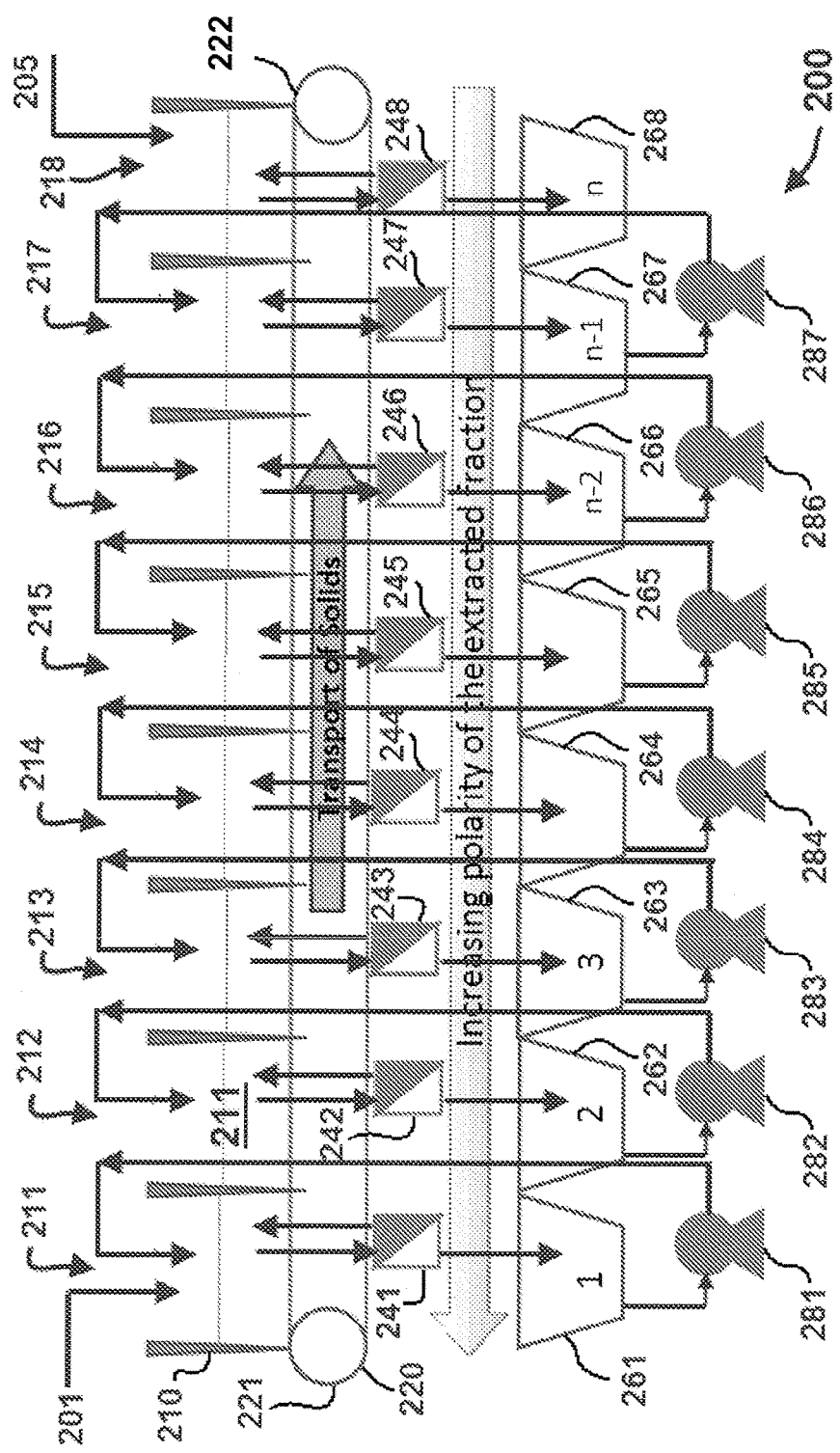
FIG. 2 is a schematic diagram of an exemplary embodiment of an extraction system according to the present disclosure.

FIG. 2 is a schematic diagram of an exemplary embodiment of an extraction system 200. The wet or dry algal biomass is transported using methods known in the art, including, but not limited to a moving belt, a screw conveyor, or through extraction chambers. The solvent for extraction is recirculated from a storage tank assigned to each biomass slot position. The extraction mixture is filtered, returning the biomass solids back into the slot and the extract into the storage tank. The solids on the belt move periodically based on the residence time requirement for extraction. The extracts in each storage tank may either be replenished at saturation or continuously replaced by fresh solvent. This would also reduce the downstream processing time and cost drastically. This embodiment comprises a primary reservoir 210, a transport mechanism 220, a plurality of separation devices 241-248 (e.g., membrane filtration devices), a plurality of extraction reservoirs 261-268, and a plurality of recycle pumps 281-287. In this embodiment, primary reservoir 210 is divided up into a plurality of inlet reservoirs 211-218.

During operation, algal biomass 201 is placed a first inlet reservoir 211 near a first end 221 of transport mechanism 220. In addition, solvent 205 is placed into inlet reservoir 218 near a second end 222 of transport mechanism 220. Transport mechanism 220 directs the algal biomass along transport mechanism 220 from first end 221 towards second end 222. As the algal biomass is transported, it passes through the plurality of separation devices 241-248 and is separated into fractions of varying polarity. The diffusate portions that pass through separation devices 241-248 are directed to reservoirs 261-268.

For example, the diffusate portion of the algal biomass that passes through the first separation device 241 (e.g., the portion containing liquid and particles small enough to pass through separation device 241) is directed to the first reservoir 261. From first reservoir 261, the diffusate portion can be recycled back to first inlet reservoir 201. The retentate portion of the algal biomass that does not pass through first separation device 241 can then be directed by transport mechanism 220 to second inlet reservoir 212 and second separation device 242, which can comprise a finer separation or filtration media than the first separation device 241.

The segment of the diffusate portion that passes through second separation device 242 can be directed to second reservoir 262, and then recycled back to second inlet reservoir 212 via recycle pump 282. The retentate or extracted portion of the algal biomass that does not pass through second separation device 242 can be directed by transport mechanism 220 to third inlet reservoir 213. This process can be repeated for inlet reservoirs 213-218 and separation devices 243-248 such that the retentate portions at each stage are directed to the subsequent inlet reservoirs, while the diffusate portions are directed to the recycle reservoirs and recycled back to the current inlet reservoir.

In exemplary embodiments, the first fraction will be extracted with the highest water to slightly nonpolar solvent ratio, i.e., most polar mixture, while the last fraction will be extracted with the most pure slightly nonpolar solvent, i.e. the least polar mixture. The process therefore extracts components in the order of decreasing polarity with the fraction. The function of the first fraction is to remove the residual water and facilitate the solvent extraction process. The fractions that follow are rich in polar lipids, while the final fractions are rich in neutral lipids.

The oil fraction can be esterified to liberate the long chain unsaturated fatty acids. The carotenoids and long chain unsaturated fatty acids can be separated from the oil using processes such as molecular distillation in conjunction with non-molecular distillation. All of the fatty acids can be separated from the carotenoids using the molecular distillation. The distillates can be fractionated using a simple distillation column to separate the lower chain fatty acids for refining. The long chain unsaturated fatty acids remain as high boiling residue in the column.

In some non-limiting embodiments, the extraction system and methods described herein incorporate one or more steps to isolate protein material from the oleaginous material (e.g., algal biomass). Such protein extraction steps employ pH adjustment(s) to achieve isolation and extraction of protein. For example, in one non-limiting embodiment, the pH of the solvent in the first separation device is optimized for protein extraction, resulting in a first fraction that is rich in protein material. The pH of the protein extraction step is adjusted depending on the pKa of the proteins of interest. The pKa of a protein of interest may be ascertained using methods known to one of skill in the art, including, but not limited to using the Poisson-Boltzmann equation, empirical methods, molecular dynamics based methods, or the use of titration curves.

In some embodiments, the solvent pH is alkaline. For example, in some embodiments, the solvent pH is greater than about 10. In other embodiments, the solvent pH ranges from about 10 to about 12. In further embodiments, the solvent pH is about 10, about 11, or about 12. In other embodiments, the solvent pH is acid. For example, in some embodiments, the solvent pH is less than about 5. In other embodiments, the solvent pH ranges from about 2 to about 5. In further embodiments, the solvent pH is about 2, about 3, about 4, about 4.5, or about 5. The extracted portion of the first separation device is then directed to subsequent inlet reservoirs to achieve extraction and fractionation based on polarity. In another non-limiting embodiment, protein material is separated in the final separation device by similar means (i.e., solvent pH adjustment).

Adjustment of solvent pH is accomplished in accordance with methods known to those of skill in the art. For example, acid pH is achieved by mixture of an appropriate acid into the solvent stream. Exemplary acids useful for protein extraction include, without limitation, phosphoric acid, sulfuric acid, and hydrochloric acid. Similarly, alkaline pH is achieved by addition and mixture of an appropriate base into the solvent stream. Exemplary bases useful for protein extraction include, without limitation, potassium hydroxide, and sodium hydroxide.

In some embodiments, protein extraction is performed in a system separate from the extraction and fractionation system described herein. For example, in some embodiments, an algal biomass is soaked in a pH-adjusted solvent mixture, followed by isolation via an appropriate separation technique (e.g., centrifugation, or filtration). The remaining solid is then introduced into an extraction and fractionation system based on polarity, as described herein. Similarly, in some embodiments, the remaining extract from an extraction and fractionation process based on polarity is exposed to a pH-adjusted solvent mixture to isolate protein material at the end of the extraction process.

Figure 3:
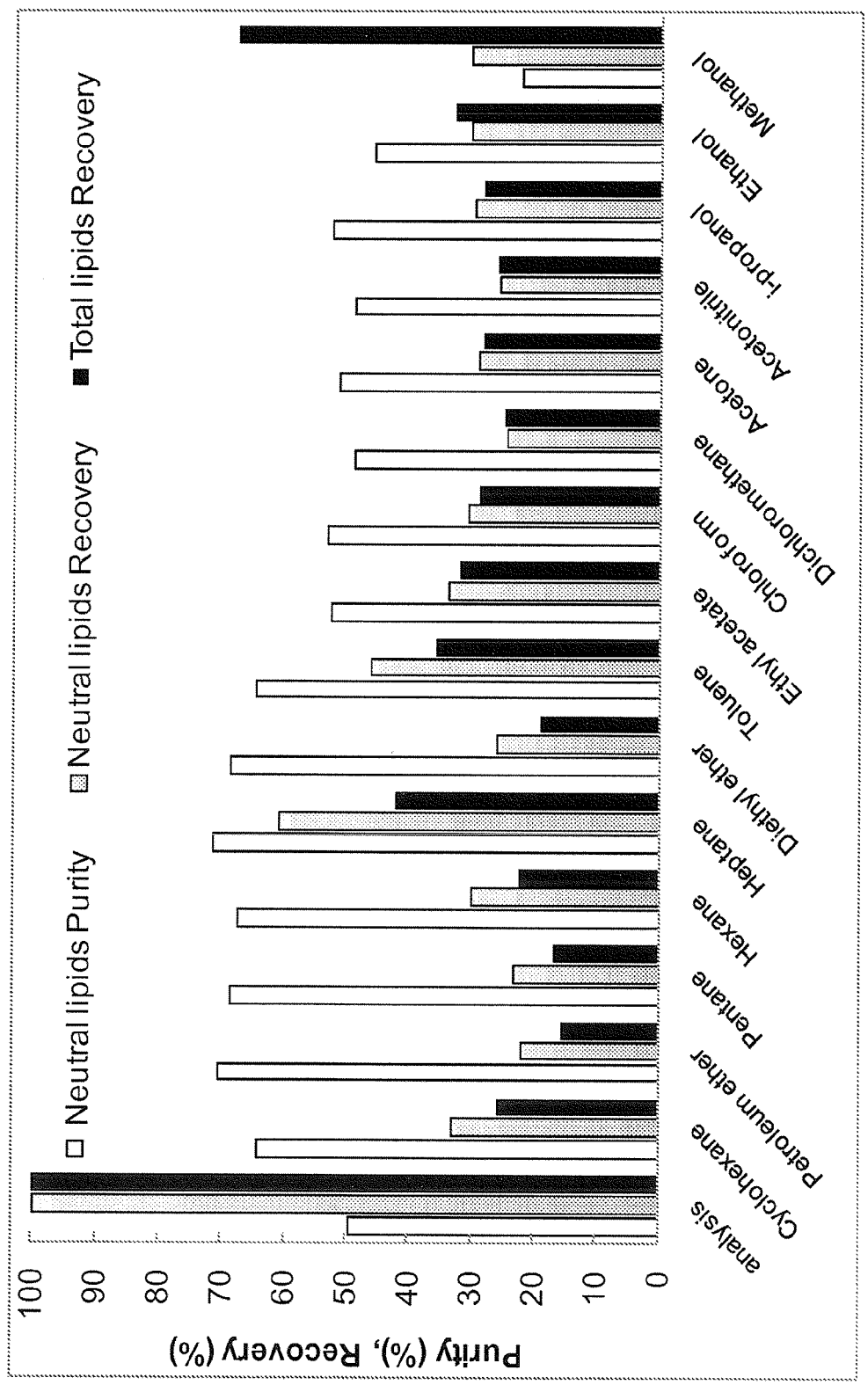
FIG. 3 is a comparative graph showing Sohxlet extraction of freeze dried algae biomass using an array of solvents encompassing the complete polarity range showing maximum non-disruptive algae oil extraction efficiency and the effect of polarity on the polar and non-polar lipids extraction.

As shown in FIG. 3, the solvent selection and the theory of fractionation based on polarity were developed by extensive analysis of solvents and the effect on extraction using the Sohxlet extraction process, which allows the separation of lipids from a solid material. The Sohxlet extraction system was utilized for rapid screening solvents for lipid class selectivity and recovery. Solvents from various chemical classes encompassing a wide range of polarities such as alkanes, cycloalkane, alkyl halides, esters, ketones, were tested. Prior to the extraction, the lipid content and composition of the biomass to be extracted was tested in triplicate using the standard methods for algae oil estimation such as the Bligh-Dyer lipid extraction method. The biomass contained 22.16% total lipid, of which 49.52% was neutral lipid.

FIG. 3 presents the data gathered by extraction of a dry algal mass using various polar and nonpolar solvents combined with a Sohxlet extraction process. Depending on the chain length of the alkane solvent, 60-70% purity of neutral lipids and 15-45% of total lipid recovery can be achieved without disruption and solvent extraction. The longest chain alkane solvent tested, heptane, recovered 60% of the neutral lipids and 42% of the total lipid. As FIG. 3 shows, the results of extraction of dry algal mass using solvents and conventional extraction methods such as hexane are inefficient, expensive, and result in poor yields. The systems and methods discloses herein address these inefficiencies by controlling the proportion of slightly nonpolar solvent to water in order to separate out components of differing polarities with minimal loss of components.

The lower carbon alcohol solvents were more selective for polar lipids. The neutral lipid purity was 22% for methanol and 45% for ethanol. Isopropyl alcohol did not show any selectivity between polar and nonpolar lipids, resulting in a 52% pure neutral lipid product. Methanol recovered 67% of the total lipids and more than 90% of the polar lipids. Therefore, methanol is an excellent candidate for an embodiment of the present invention wherein methanol can be used to selectively extract polar lipids from an oleaginous material prior to extracting the neutral lipids using heptane or hexane. The other solvent classes tested did not show any selectivity towards lipid class since the neutral lipid purity was close to 49%, similar to the lipid composition present in the original biomass. Furthermore, the total lipid recovery achieved with these solvents ranged from about 15-35%, rendering these solvents unsuitable for the selective extraction of particular lipid classes or total lipid extraction.

The results from the Sohxlet analysis were confirmed using the standard bench scale batch solvent extraction apparatus described below in Example 1. The solvents selected were methanol for the first step to recover polar lipids, and petroleum ether in the second step for recovery of neutral lipids. All of the extractions were performed with a 1:10 solid:solvent ratio. Each extraction step in this experiment was 1 hour long. Other experiments done (data not shown) indicate that about 45 minutes or longer is long enough for the extraction to be successful. This retention time is dependent on the heat and mass transfer of the system.

The methanol extractions were performed at different temperatures, 40° C., 50° C., and 65° C., in order to determine which was optimal. The petroleum ether extraction was performed at 35° C., close to the boiling point of the solvent. Petroleum ether was chosen because of its high selectivity for neutral lipids, low boiling point, and the product quality observed after extraction.

Figure 4A:
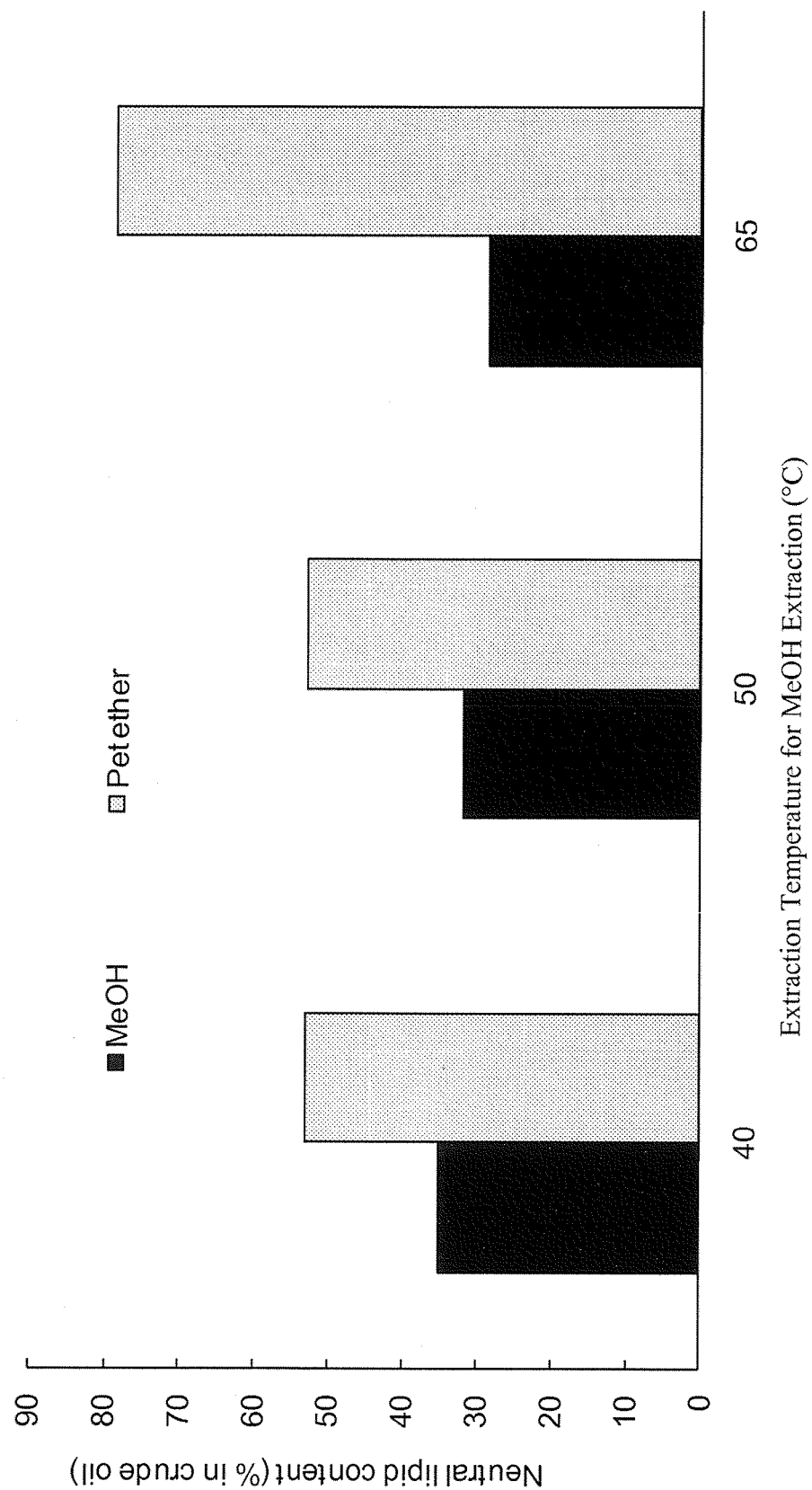
FIGS. 4A&B are graphic representations showing neutral lipids (A) Purity and (B) Recovery in the two step solvent extraction process using methanol and petroleum ether at three different temperatures.
Figure 4B:
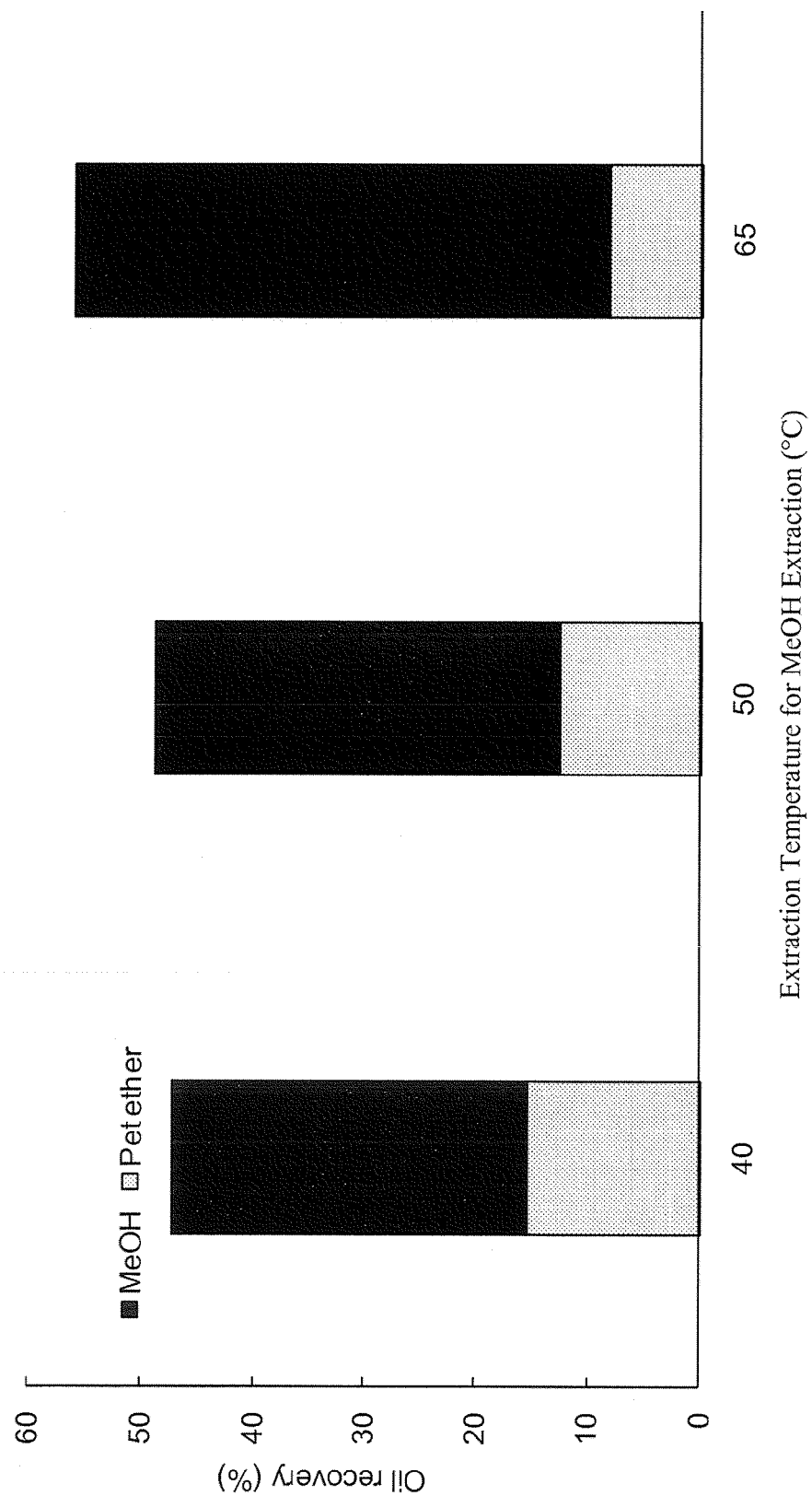

FIG. 4A shows that the neutral lipid purity in a petroleum ether extraction carried out after a methanol extraction step at 65° C. is over 80%, demonstrating that the combination of these two extraction steps enhanced the neutral lipid content of the final crude oil product. FIG. 4B shows that the total neutral lipid recovery was low and there was a significant amount of neutral lipid loss in the first step.

Figure 5A:
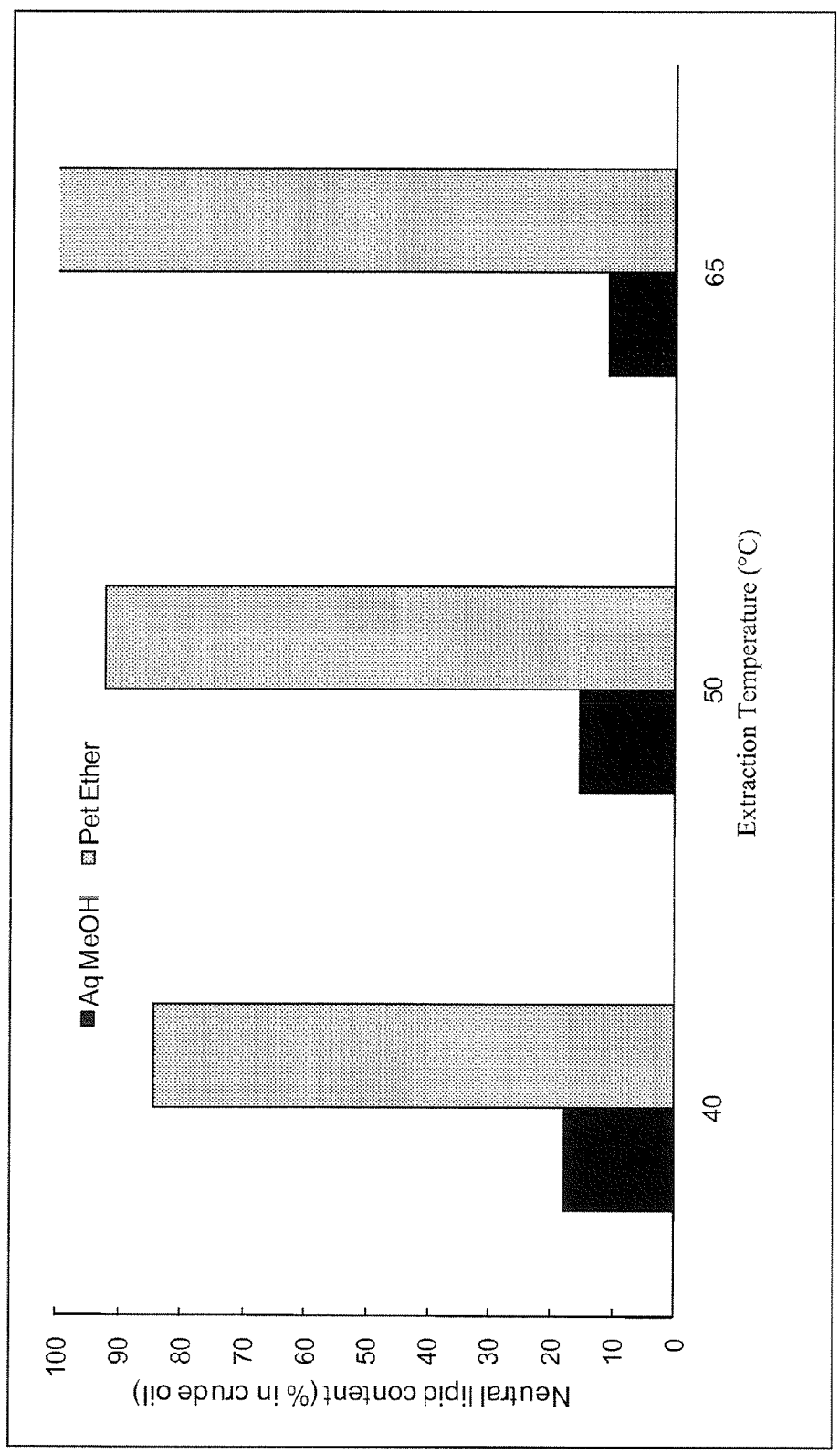
FIGS. 5A&B are graphs showing neutral lipids (A) Purity and (B) Recovery in the two step solvent extraction process using aqueous methanol and petroleum ether at three different temperatures.
Figure 5B:
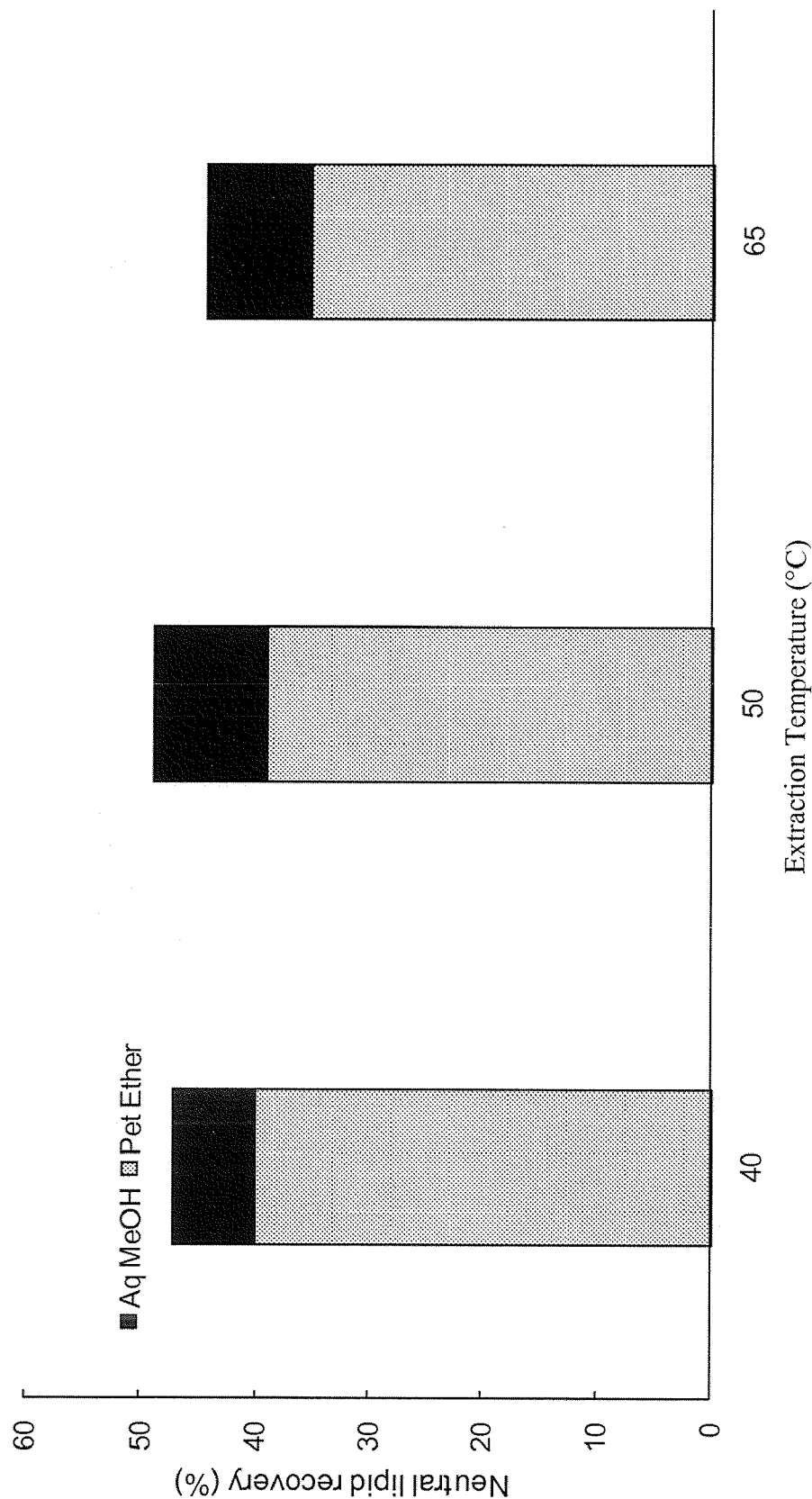

To minimize the loss of neutral lipids in the methanol extraction step, the polarity of the solvent can be increased by adding water to the solvent. FIGS. 5A and 5B show the results of extracting the aforementioned biomass with 70% v/v aqueous methanol followed by extraction with petroleum ether. FIG. 5A shows that the neutral lipid purity was much higher in the petroleum ether extraction than was achieved by the use of pure methanol. Moreover, the loss of neutral lipids was greatly reduced by the use of aqueous methanol in the first extraction step. As seen in FIG. 5B, methanol extraction at higher temperatures improved neutral lipid purity but slightly decreased the total lipid recovery in the subsequent step.

In some exemplary embodiments the temperature of the extraction process is controlled in order to ensure optimal stability of algal components present in the algal biomass. Algal proteins, carotenoids, and chlorophyll are examples of algal components that exhibit temperature sensitivity. In other embodiments, the temperature is increased after the temperature sensitive algal components have been extracted from the algal biomass.

In still other exemplary embodiments, the temperature of the extraction process is adjusted in order to optimize the yield of the desired product. Extractions can be run from ambient temperature up to, but below, the boiling point of the extraction mixture. In still other embodiments, the temperature of the extraction process is changed depending on the solubility of the desired product. In still other embodiments, the extraction temperature is optimized depending on the algal strain of the biomass to be extracted. Elevated extraction temperatures increase the solubility of desired compounds and reduce the viscosity of the extraction mixture enhancing extraction recovery.

In some embodiments, the extraction is run under pressure to elevate the boiling point of the extraction mixture. In these implementations, the pressure is increased to the degree necessary to prevent boiling, while maintaining the temperature of the extraction mixture below a temperature at which any of the desired products would begin to degrade, denature, decompose, or be destroyed.

In some exemplary embodiments, the extraction is performed near the boiling point of the solvent used, at the conditions under which the extraction is performed (e.g., atmospheric or elevated pressures). In other embodiments, the extraction is performed near the boiling point of the extraction mixture, again accounting for other extraction conditions. At such temperatures, vapor phase penetration of the solvent into the algal cells is faster due to lower mass transfer resistance. If the extraction temperature is allowed to significantly exceed the boiling point of the solvent, the solvent-water system can form an azeotrope. Thus, maintaining the system at or near the boiling point of solvent would generate enough vapors to enhance the extraction, while reducing expense. In addition, the solubility of oil is increased at higher temperatures, which can further increase the effectiveness of extraction at temperatures close to the solvent boiling point.

Figure 6:
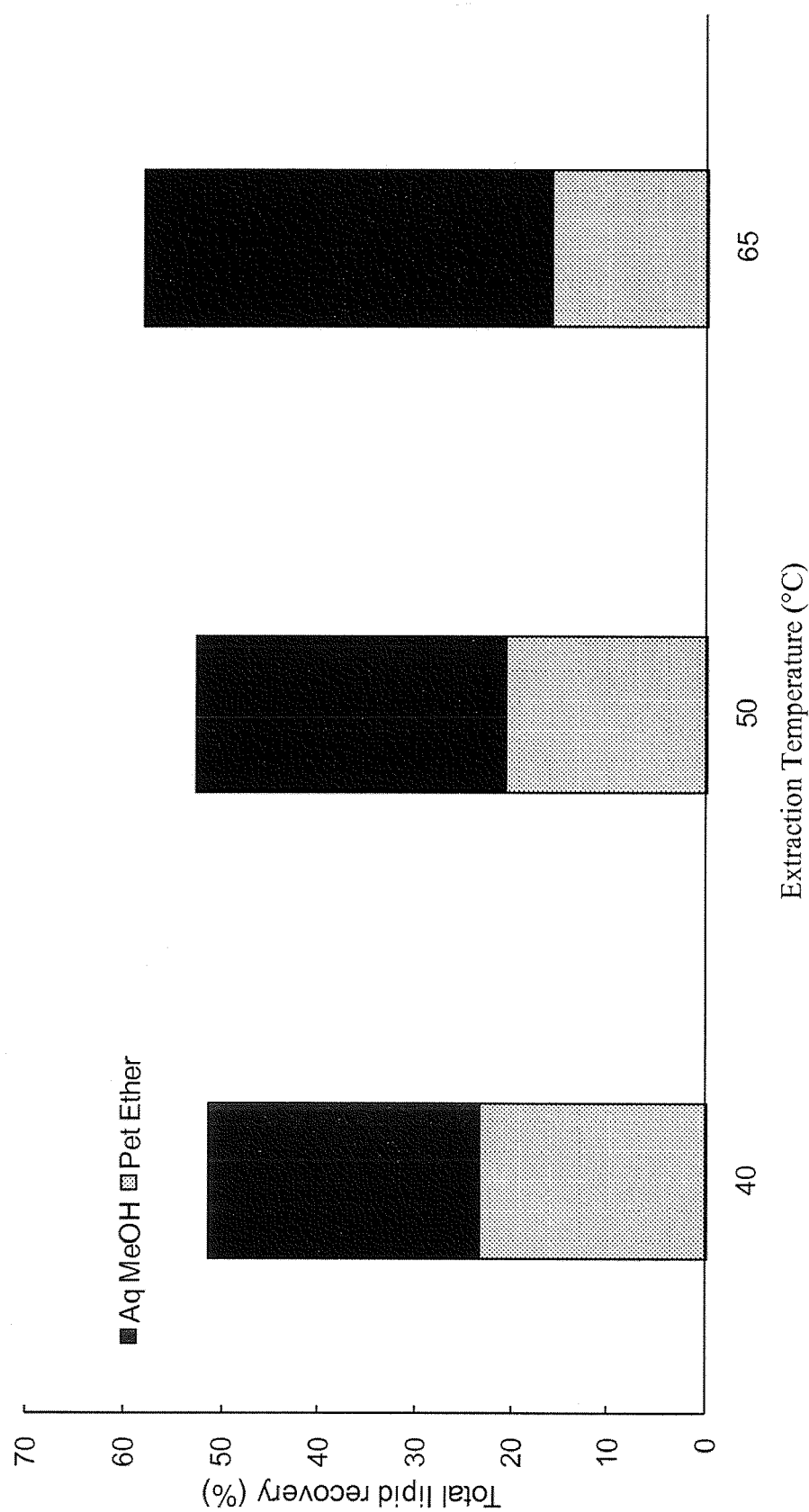
FIG. 6 is a graph showing lipid recovery in the two step solvent extraction process using aqueous methanol and petroleum ether at three different temperatures.

FIG. 6 shows the total lipid recovery in the aqueous methanol-petroleum ether extraction scheme. Although performing the methanol extraction near its boiling temperature slightly decreases the neutral lipid recovery as observed in FIG. 5B, it enhances the total lipid recovery.

In other embodiments, the extraction is carried out under ambient lighting conditions. In other embodiments, the extraction is carried out in an opaque container such as, but not limited to, a steel tube or casing, in order to protect light sensitive algal components from degradation. Carotenoids are light sensitive algal components.

In other exemplary embodiments, the extraction takes place under normal atmospheric conditions. In still other embodiments, the extraction takes place under a nitrogen atmosphere in order to protect algal components prone to oxidation. In still other embodiments, the extraction takes place under an atmosphere of inert gas in order to protect algal components prone to oxidation. Algal components that might be prone to oxidation include carotenoids, chlorophyll, and lipids.

In exemplary embodiments, the solvent-to-solid ratio for the extraction is between 3-5 based on the dry weight of the solids in the biomass. The residual algal biomass is rich in carbohydrates (e.g., starch) and can be used as a feed stock to produce the solvent used for extraction.

Figure 7:
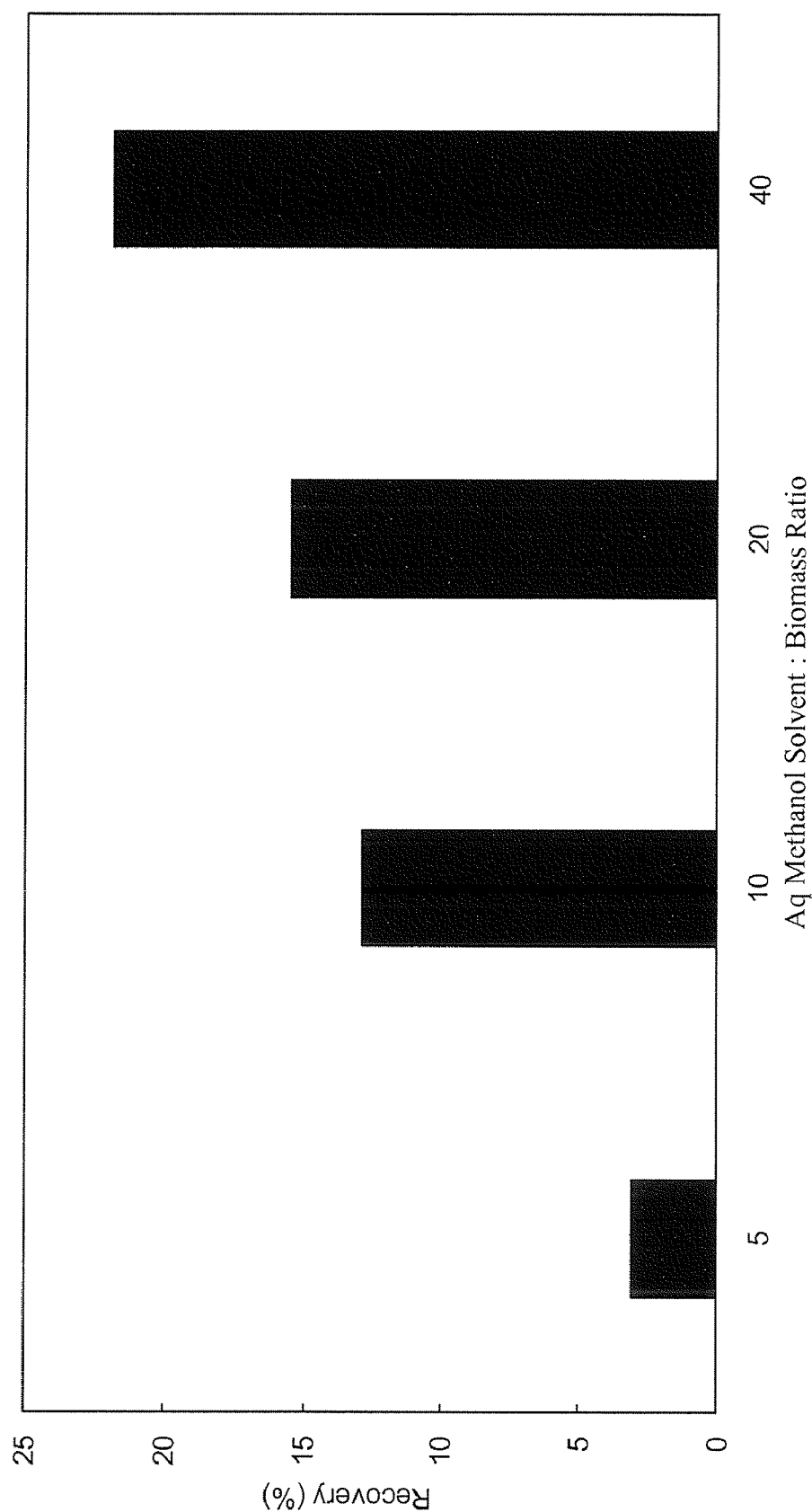
FIG. 7 is a graph showing the effect of solvents to solid biomass ratio on lipid recovery.

FIG. 7 shows the effect of the solvent to solid ratio on the total lipid recovery. As the solvent to solid ratio was increased, there was a corresponding and drastic increase in total lipid recovery. It is believed that this was because of the lower solubility of lipids in methanol as compared to other commonly used oil extraction solvents such as hexane.

The solubility of components is affected by the polarity of solvent used in an extraction process. The solubility properties can be used to determine the ratio of wet biomass to solvent. For example, a 40% w/w wet biomass has 40 g biomass and 60 g water for every 100 g of wet biomass. If 100 g of ethanol is added to this mixture, the ratio of ethanol to wet biomass is 1 part wet biomass to 1 part ethanol and the concentration of ethanol in the mixture is 100/(100+60) equals about 62% w/w of ethanol in the liquid phase. 62% w/w of ethanol in ethanol water mixture corresponds to a polarity index of 6.6, calculated by weight and averaging the polarities of the components. Ethanol, having a polarity index of 5.2, and water, having a polarity index of 9, in a mixture containing 62% ethanol and 38% water results in a polarity index of (0.62*5.2+0.38*9) about 6.6. The polarity index of the mixture for extraction of polar lipids and neutral lipids is calculated to be about 5.8 and 5.4 respectively. In light of the instant disclosure, one of skill in the art would be able to formulate a solvent set that can selectively extract these components.

In another example, if the extraction solvent is a 1:1 mixture of isopropyl alcohol and ethanol, the polarity of this solvent is ((3.9+5.4)/2) which is about 4.65. The ratio of solvent to wet biomass would be calculated to match the polarities. To get a 6.6 polarity index, we would need to make a 55% w/w of IPA-water mixture calculated by solving the following algebraic equation:

$$x * 4.65 + (1 - x) * 9 = 6.6$$

-continued $$x = (9 - 6.6)/(9 - 4.65) = 0.55$$

↓

55% w/w of solvent mix in solvent mix-water

↓

For a 40% w/w wet biomass, the wet biomass to IPA ratio is
(1 − 0.55)/0.6~0.75

With a 40% w/w wet biomass this would correspond to a ratio of 100 parts wet biomass to 75 parts solvent mixture. A 40% w/w wet biomass has 40 g biomass and 60 g water for every 100 g of wet biomass. If 75 g of solvent mixture is added to this mixture, the concentration of solvent in the mixture is (75/(75+60)) is about 55% w/w of solvent mixture in the solvent mixture-water solution. This calculation can be used to obtain the solvent biomass ratio at each extraction stage and for each product. A few nonlimiting examples of solvent sets appear in Table 3.

TABLE 3

| | parts wet biomass | parts solvent | Biomass dryness | Parts Dry Biomass | Parts Water | Solvent-water ratio | Extraction solvent polarity index |
|---|---|---|---|---|---|---|---|
| One step Protein Extraction | | | | | | | |
| Ethanol | 100 | 99 | 40% | 40 | 60 | 0.62 | 5.2 |
| IPA | 100 | 52 | 40% | 40 | 60 | 0.46 | 3.9 |
| MeOH | 100 | 93 | 40% | 40 | 60 | 0.61 | 5.1 |
| Propanol | 100 | 54 | 40% | 40 | 60 | 0.47 | 4 |
| 1:1 IPA EtOH mixture | 100 | 68 | 40% | 40 | 60 | 0.53 | 4.55 |
| 95% ethanol water mixture | 100 | 115 | 40% | 40 | 60 | 0.66 | 5.39 |
| 95% ethanol 5% methanol mixture | 100 | 99 | 40% | 40 | 60 | 0.62 | 5.195 |
| 95% ethanol 5% IPA mixture | 100 | 95 | 40% | 40 | 60 | 0.61 | 5.135 |
| One step Polar lipids Extraction | | | | | | | |
| Ethanol | 100 | 320 | 40% | 40 | 60 | 0.84 | 5.2 |
| IPA | 100 | 101 | 40% | 40 | 60 | 0.63 | 3.9 |
| MeOH | 100 | 274 | 40% | 40 | 60 | 0.82 | 5.1 |
| Propanol | 100 | 107 | 40% | 40 | 60 | 0.64 | 4 |
| 1:1 IPA EtOH mixture | 100 | 154 | 40% | 40 | 60 | 0.72 | 4.55 |
| 95% ethanol water mixture | 100 | 468 | 40% | 40 | 60 | 0.89 | 5.39 |
| 95% ethanol 5% methanol mixture | 100 | 317 | 40% | 40 | 60 | 0.84 | 5.195 |
| 95% ethanol 5% IPA mixture | 100 | 289 | 40% | 40 | 60 | 0.83 | 5.135 |
| One step Neutral lipids Extraction | | | | | | | |
| Ethanol | 100 | 1,080 | 40% | 40 | 60 | 0.95 | 5.2 |
| IPA | 100 | 144 | 40% | 40 | 60 | 0.71 | 3.9 |
| MeOH | 100 | 720 | 40% | 40 | 60 | 0.92 | 5.1 |
| Propanol | 100 | 154 | 40% | 40 | 60 | 0.72 | 4 |
| 1:1 IPA EtOH mixture | 100 | 254 | 40% | 40 | 60 | 0.81 | 4.55 |
| 95% ethanol water mixture | 100 | 21,600 | 40% | 40 | 60 | 1.00 | 5.39 |
| 95% ethanol 5% methanol mixture | 100 | 1,054 | 40% | 40 | 60 | 0.95 | 5.195 |
| 95% ethanol 5% IPA mixture | 100 | 815 | 40% | 40 | 60 | 0.93 | 5.135 |

The extraction mixture described in all examples, is made up of a substantially solid phase and a substantially liquid phase. These phases are then separated post extraction. This can then be followed by removal of the liquid solvent from the liquid phase, yielding an extraction product. In some embodiments, the solvent is evaporated. In such an implementation, a liquid-liquid extraction technique can be used to reduce the amount of solvent that needs to be evaporated. Any solvents used can be recycled if conditions allow.

Figure 8:
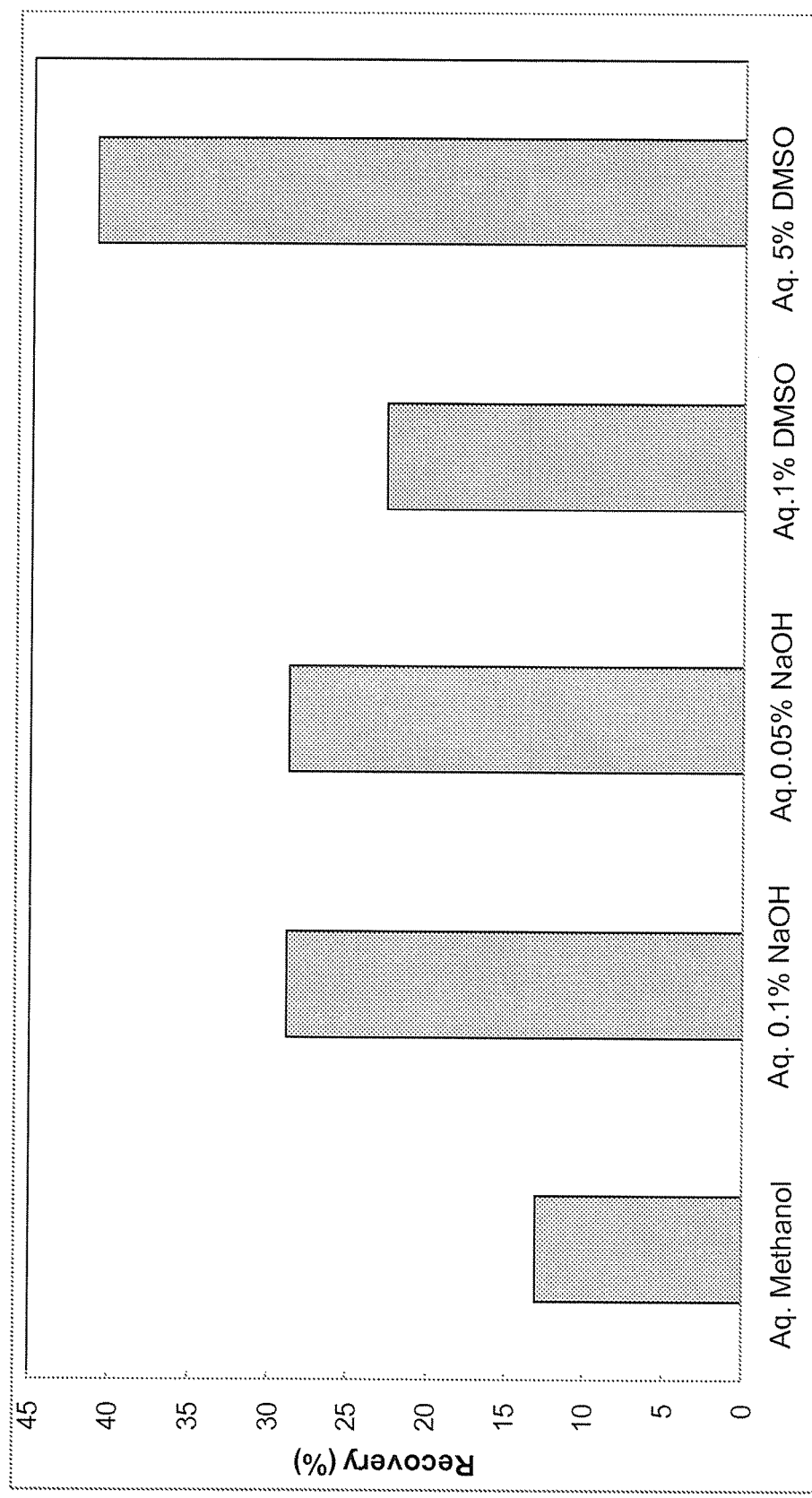
FIG. 8 is a graph showing the efficacy of different aqueous extraction solutions in a single step extraction recovery of aqueous methanol on dry biomass.

It was theorized that treatment of the algal biomass prior to extraction would enhance the productivity and efficiency of lipid extraction. In this direction an experiment was done comparing the effect of adding a base or another organic solvent to an algal biomass to change the surface properties and enhance extraction. A variety of treatments including aqueous methanol, aqueous sodium hydroxide, and aqueous DMSO were attempted. As FIG. 8 demonstrates, the addition of 5% DMSO increases the lipid recovery 3-fold. These extraction steps may be exploited to dramatically reduce the methanol extraction steps. However, the solutions used in the above experiments may not be ideal for use on larger scales due to the high cost, viscosity, and ability to recover and recycle DMSO.

Figure 9:
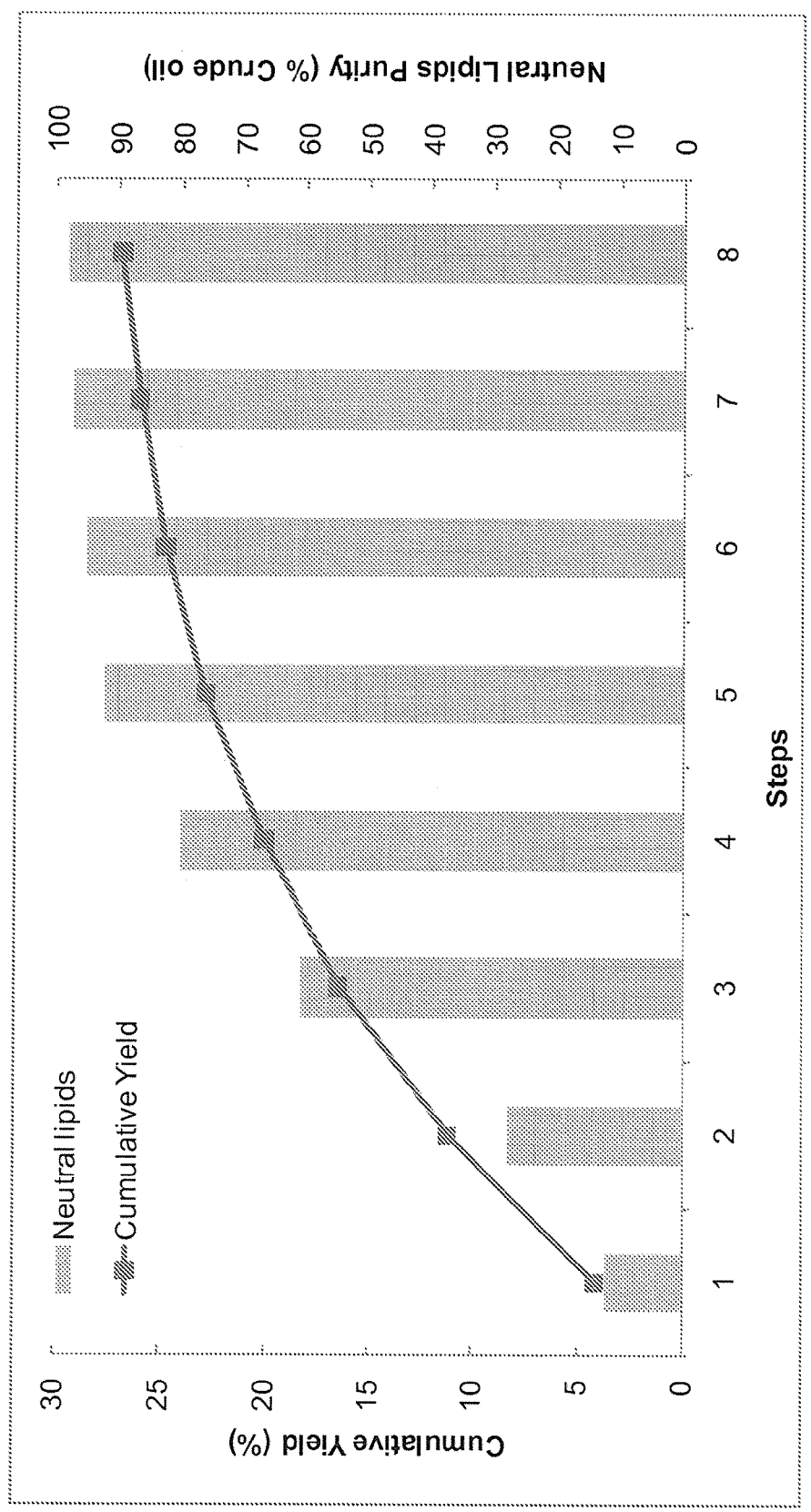
FIG. 9 is a graph showing the effect of multiple step methanol extractions on the cumulative total lipid yield and the neutral lipids purity.

FIG. 9 is a chart showing the effect of an eight step methanol extraction on the cumulative total lipid yield and the purity of the extracted neutral lipid. In this embodiment, 112 grams of wet biomass (25.6% dry weight), was extracted with 350 mL pure methanol and heating for 10 minutes at 160 W irradiance power in each step. This resulted in an extraction temperature of about 75° C., which was near the boiling point of the extraction mixture. Using this process, it was determined that it is possible to obtain highly pure neutral lipids from algal oil once the majority of the polar lipids have been extracted. FIG. 9 shows that it is possible to isolate high purity neutral lipid once the polar lipids are all extracted. In this case a 5% yield of total biomass was achieved with over 90% neutral lipids purity in methanol extraction steps 5 through 8. Furthermore, due to the boiling point of the extraction mixture, most of the water in the biomass is completely extracted in the first extraction step, along with carbohydrates, proteins and metals.

Figure 10:
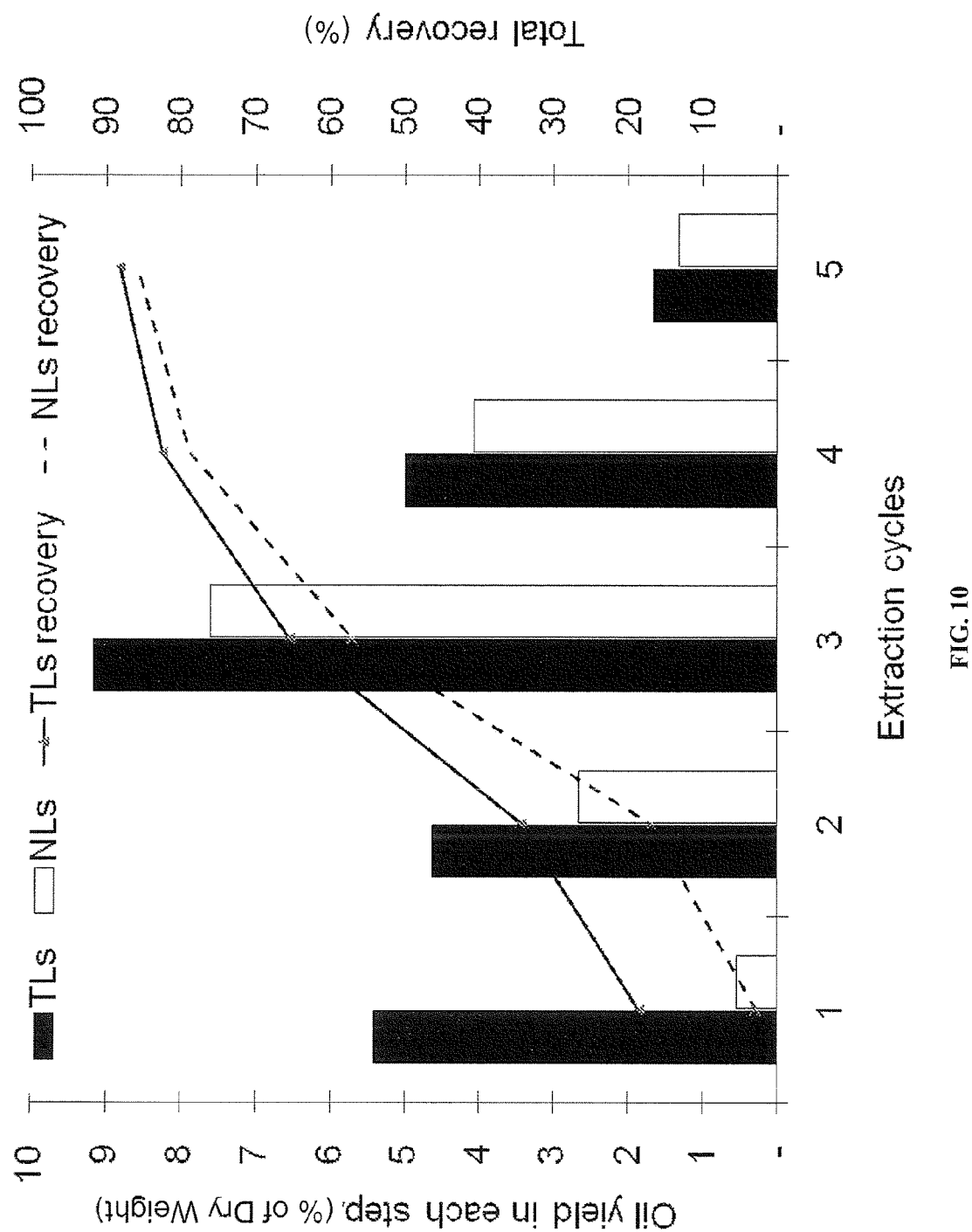
FIG. 10 is a graph showing the cumulative recovery of lipids using wet biomass and ethanol.

FIG. 10 shows that recovery of lipids can be made more efficient by the use of ethanol to extract lipids and protein from wet biomass. By using ethanol, 80% total lipid recovery can be achieved in about 4 steps rather than the 9 generally needed by using methanol. This increase in recovery may be attributed to greater solubility of lipids in ethanol as compared to methanol. Furthermore, the boiling point of aqueous ethanol is higher than aqueous methanol, facilitating further recovery of lipids. This is because the higher temperature renders the oil less viscous, thereby improving diffusability. Another distinct advantage of this process is using the residual ethanol in the oil fraction for transesterification as well as lowering the heat load on the biomass drying operation.

Further, FIG. 10 demonstrates that the initial fractions are non-lipid rich, containing proteins and other highly polar molecules, followed by the polar lipid rich fractions and finally the neutral lipid fractions. Hence with a proper design of the extraction apparatus, one can recover all the three products in a single extraction and fractionation process.

Another embodiment of the current invention utilizes microwaves to assist extraction. Based on previously gathered data disclosed in this application, it is shown that methanol is the best single solvent for extraction of all lipids from algae. Hence, a single solvent multiple step extraction, as described in Example 1 of the instant application, was performed in order to gather data on the efficacy of a one solvent microwave extraction system.

Figure 11:
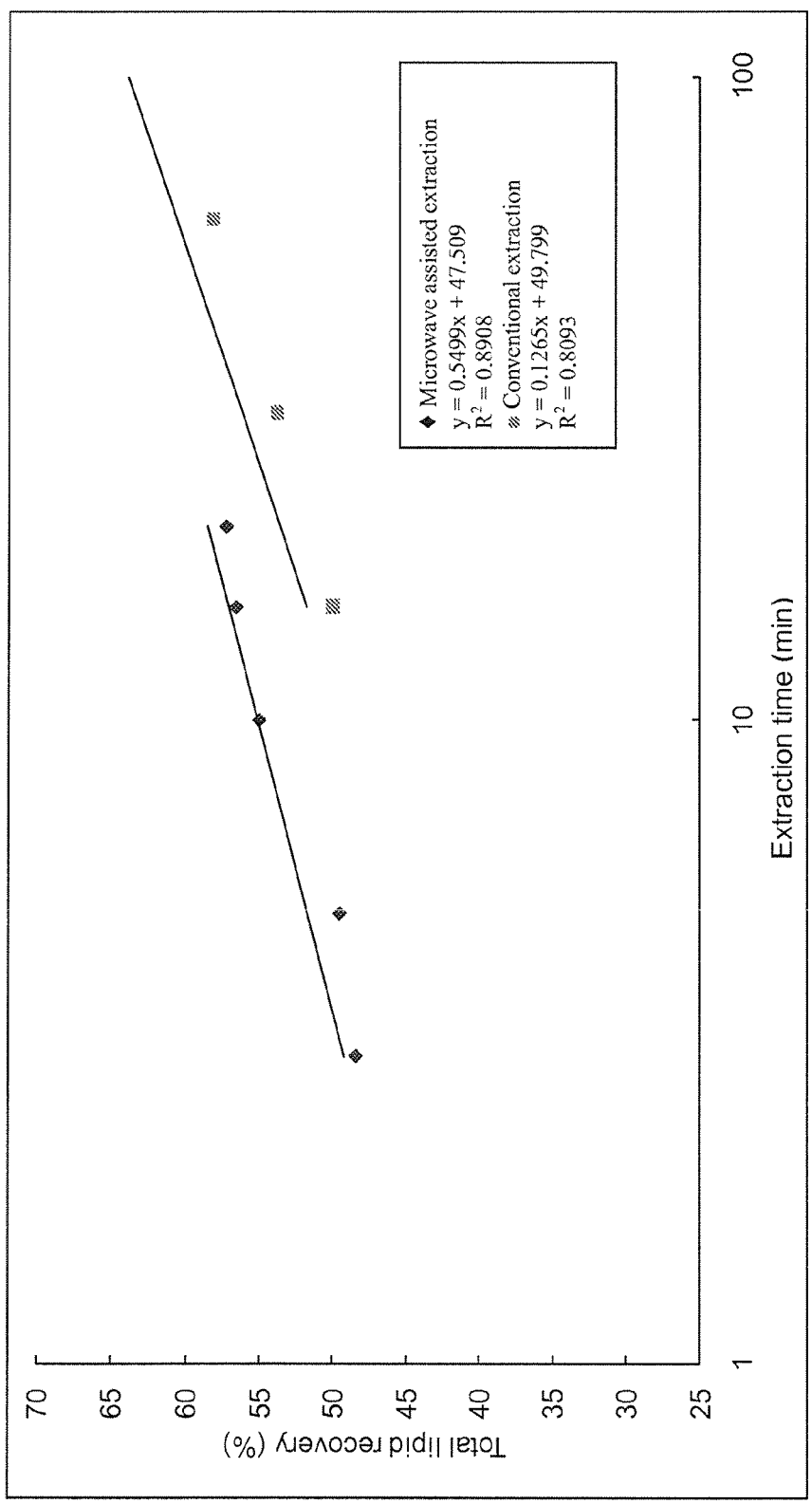
FIG. 11 is a graph showing a comparison of the extraction times of the microwave assisted extraction and conventional extraction systems.

FIG. 11 is a logarithmic plot comparing the extraction time and total lipid recovery of conventional extraction and microwave-assisted extraction. Based on the slope of the curve, it was calculated that the microwave system reduces the extraction time by about five fold or more. While the conventional methods have a higher net lipid recovery, this is due to higher recoveries of polar lipids. Based on these results, the conditions for extraction of dry algal biomass using solvents with and without microwave assistance have been optimized. Some embodiments of the invention use traditional microwave apparatus, which emit wavelengths that excite water molecules. Further embodiments of the invention utilize customized microwave apparatus capable of exciting different solvents. Still other embodiments of the invention utilize custom microwave apparatus capable of exciting the lipids present in the algal biomass. In some embodiments, the lipids present in the algal biomass are excited using microwaves, thereby enhancing the separation and extraction of the lipid components from the algal biomass.

Moisture content is another parameter of biomass that will influence the efficiency of oil extraction. In some embodiments of the present invention, dry algal mass is extracted and fractionated. In other embodiments, the algal mass is wet. Biomass samples with algae mass contents of 10%, 25%, and 33% were used to investigate the influence of moisture on extraction performance.

Figure 12A:
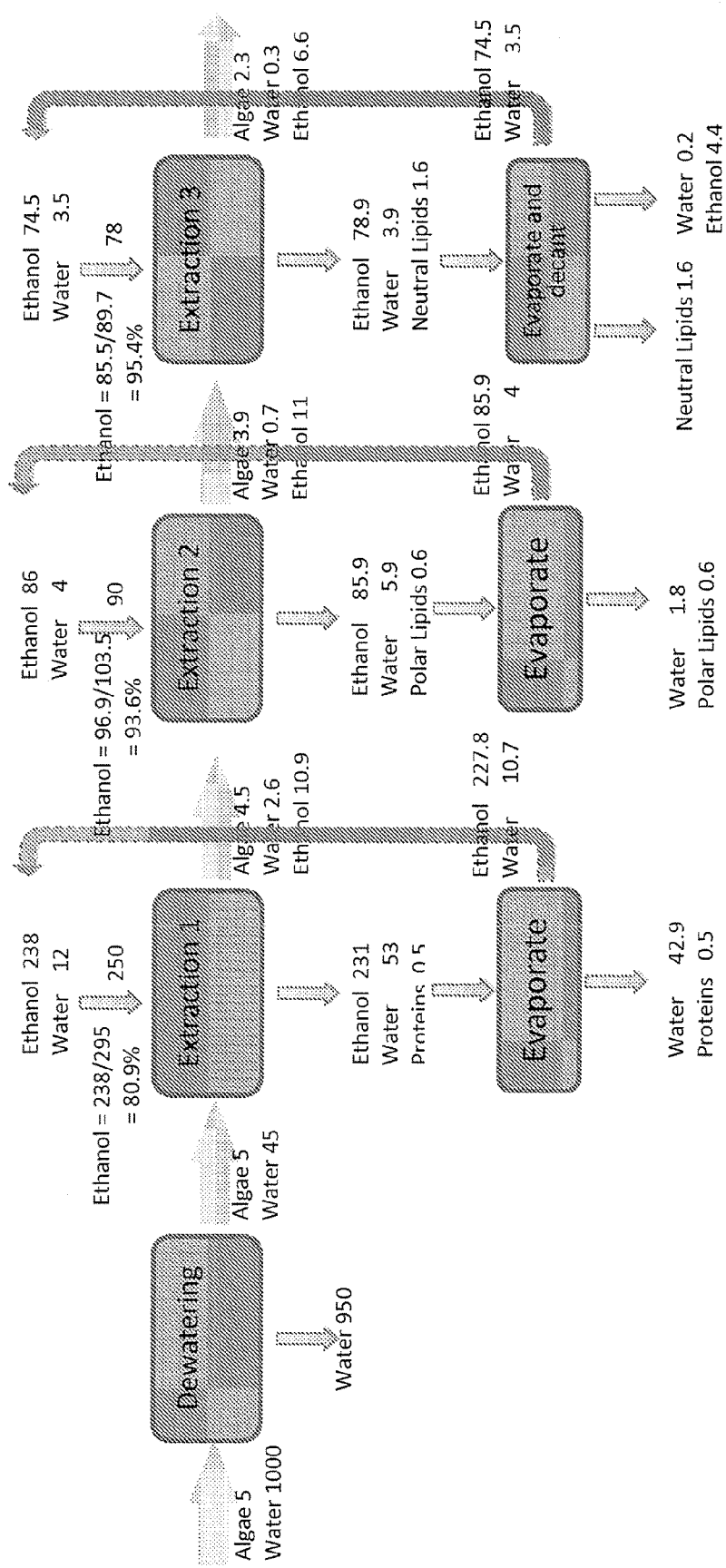
FIG. 12A is a flowchart of steps involved in a method according to an exemplary embodiment of the present disclosure which incorporates a step of protein extraction. All of the units in FIG. 12A are in pounds.

FIG. 12A shows an illustrative process 400 for a step-wise extraction of products from an algae biomass. All units in FIG. 12A are in pounds. FIG. 12A shows a mass balance of the process 400, while the details of the equipment and/or systems for performing the process are described elsewhere herein. A biomass containing 5 pounds of algae has about 0.63 pounds of polar lipids, 1.87 pounds neutral lipids, 1 pound protein, and 1.5 pounds carbohydrates. The biomass and 1000 pounds of water is processed in a dewatering step 405, which separates 950 pounds of water from the mixture and passes 5 pounds of algae in 45 pounds of water to a first extraction step 410. Any of the dewatering techniques disclosed herein can be used tin dewatering step 405. In the first extraction step 410, 238 pounds of ethanol and 12 pounds of water are combined with the algae and water from the previous step. The first extraction step 410 has a liquid phase of about 80.9% w/w ethanol. A first liquid phase of 231 pounds of ethanol, 53 pounds of water, and 0.5 pounds of algal proteins are recovered, from which water and ethanol are removed by, e.g., evaporation, leaving a protein-rich product 415. Solvent recovered from the evaporation can be recycled to the first extraction step 410.

A first solid phase from the first extraction step 410 is passed to a second extraction step 420; this first solid phase includes 4.5 pounds of algae, 2.6 pounds of water, and 10.9 pounds of ethanol. Eighty-six pounds of ethanol and 4 pounds of water are added to the first solid phase from the previous step. The second extraction step 420 has a liquid phase of about 93.6% w/w ethanol. A second liquid phase of 85.9 pounds ethanol, 5.9 pounds water, and 0.6 pounds polar lipids are recovered, from which water and ethanol are removed by, e.g., evaporation, leaving a polar lipid-rich product 425. Solvent recovered from the evaporation can be recycled to the second extraction step 420.

A second solid phase from the second extraction step 420 is passed to a third extraction step 430; this first solid phase includes 3.9 pounds of algae, 0.7 pounds of water, and 11 pounds of ethanol. Seventy-found and a half pounds of ethanol and 3.5 pounds of water are added to the second solid phase from the previous step. The third extraction step 430 has a liquid phase of about 95.4% w/w ethanol. A third liquid phase of 78.9 pounds ethanol, 3.9 pounds water, and 1.6 pounds neutral lipids are recovered, from which water and ethanol are removed by, e.g., evaporation, leaving a neutral lipid-rich product 435. Solvent recovered from the evaporation can be recycled to the second extraction step 430 A solid phase of 2.3 pounds algae, 0.3 pounds water, and 6.6 pounds ethanol remain.

As demonstrated in FIG. 12A, the resulting lipid profile with each sequential ethanol extraction step was largely influenced by the moisture content in the starting algae. Models of process 400 were run on three different biomass collections, each having a different initial water content. As the initial water content decreased, the maximum lipid recovery step changed from the third extraction step to a fourth (not shown). However, the overall lipid recovery from these three biomass samples were quite similar, all above 95% of the total lipid content of the algal biomass.

When algal mass with higher moisture content was used, the ethanol concentration in the aqueous ethanol mixture was much lower, and consequently the neutral lipid percentage in the crude extract was also lower. It has been reported that dewatering an algae paste with 90% water is a very energy intensive process. The methods described herein unexpectedly can be used to successfully extract and fractionate an algal mass containing mostly water. As overall lipid recovery was not significantly influenced by starting from an algae paste containing 90% water (10% algal solids), unlike conventional extraction methods, the methods disclosed herein do not require the use of an energy intensive drying step.

Figure 12B:
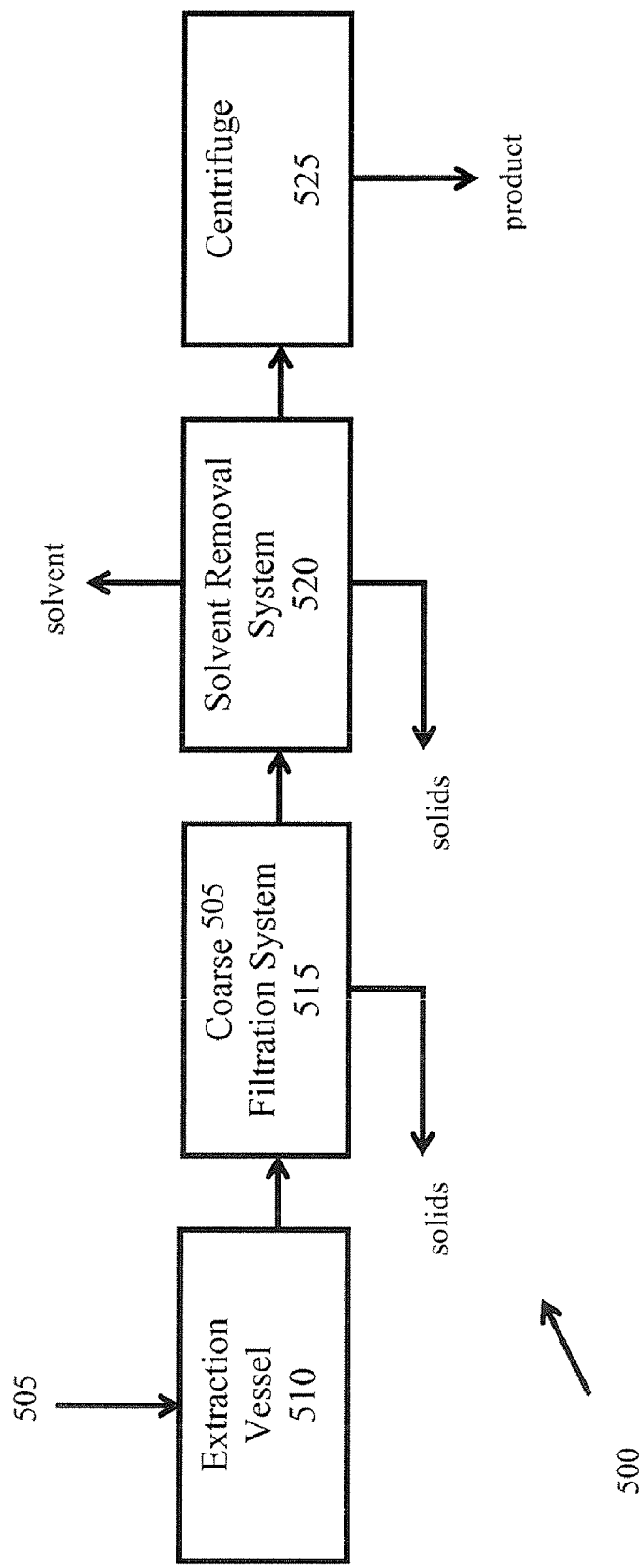
FIG. 12B is a flowchart of steps involved in an exemplary extraction process according to the present disclosure.

FIG. 12B shows an illustrative implementation 500 of one of the extraction steps of process 400. An algae biomass and solvent mixture 505 is provided to an extraction vessel 510. After the algae is extracted (as described elsewhere herein), the mixture is provided to a coarse filtration system 515, such as a sintered metal tube filter, which separates the mixture into a liquid phase and a solid phase. The solid phase is passed to a downstream extraction step. The liquid phase is passed to a solvent removal system 520, e.g., an evaporator, to reduce the solvent (e.g., ethanol) content in the liquid phase. The liquid phase remaining after solvent removal is, optionally, passed to a centrifuge 525. Any solids remaining in the solvent removal system are recycled or discarded. Centrifuge 525 assists in separating the desired algal product (e.g., proteins or lipids) from any remaining water and/or solids in the liquid phase.

Figure 14:
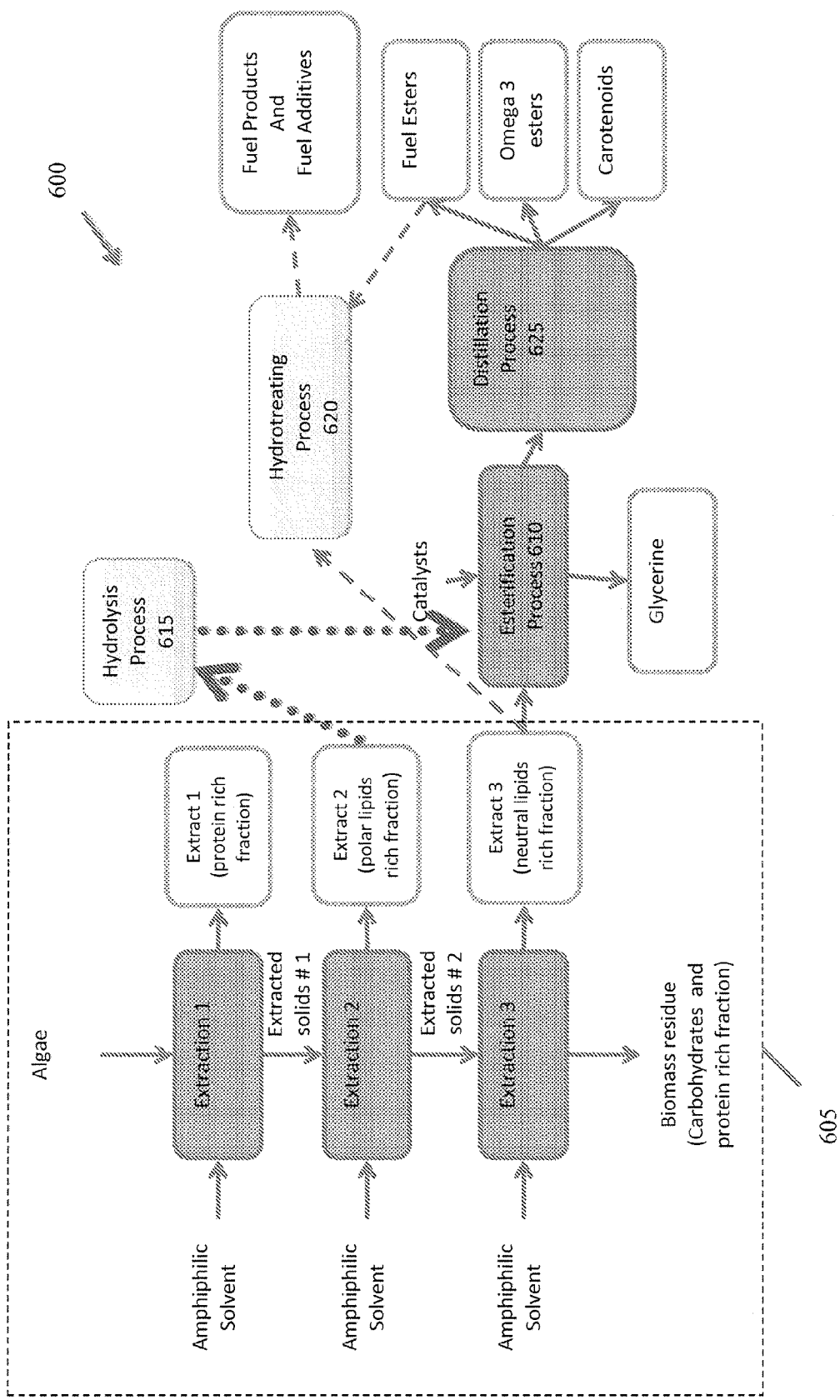
FIG. 14 is a flowchart describing one of the embodiments of the present invention wherein an algal mass can be processed to form various products.

FIG. 14 shows an example of a process 600 by which an algal mass can be processed to form or recover one or more algal products. In this example, an algal biomass is extracted in a step-wise manner in a front-end process 605 using the methods disclosed herein. The extraction and separation steps are followed by an esterification process 610, a hydrolysis process 615, a hydrotreating process 620, and/or a distillation process 625 to further isolate components and products. The components and products include algal lipids, algal proteins, glycerine, carotenoids, nutraceuticals (e.g., long chain unsaturated oils and/or esters), fuel esters (generally, the esters having chain lengths of C20 or shorter), fuels, fuel additives, naphtha, and/or liquid petroleum substitutes. In preferred embodiments the fuel esters are C16 chain lengths. In others, the fuel esters are C18 chain lengths. In still other embodiments, fuel esters are a mixture of chain lengths, C20 or shorter.

The esterification process 610, hydrolysis process 615, hydrotreating process 620, and distillation process 625 are optional and can be used in various orders. The dashed arrows and dotted arrows indicate some, but not all, of the options for when the hydrolysis, hydrotreating, and/or distillation processes may be performed in the processing of the lipid fractions. For example, in some embodiments of the invention, after extraction and/or separation are carried out, the neutral lipids fraction can be directly hydrotreated in order to make fuel products and/or additives. Alternatively, in other embodiments, the neutral lipid fraction can be passed to esterification process 610.

Esterification process 610 can include techniques known in the art, such as acid/base catalysis, and can include transesterification. Although base catalysis is not excluded for producing some products, acid catalysis is preferred as those techniques avoid the soaps that are formed during base catalysis, which can complicated downstream processing. Enzymatic esterification techniques can also be used. Esterification can process substantially pure lipid material (over 75% lipid, as used herein). After esterification, glycerine byproduct can be removed. The esterified lipids can then undergo molecular and/or nonmolecular distillation (process 625) in order to separate esterified lipids of different chain lengths as well as carotenoids present in the lipid fraction. The esterified lipids can then be passed to hydrotreating process 620 to generate jet fuel, biodiesel, and other fuel products. Any hydrotreating process known in the art can be used; such a process adds hydrogen to the lipid molecules and removes oxygen molecules. Exemplary conditions for hydrotreating comprise reacting the triglycerides, fatty acids, fatty acid esters with hydrogen under high pressure in the range of 600 psi and temperature in the range of 600° F. Commonly used catalysts are NiMo or CoMo.

Hydrotreating the fuel esters rather than the raw lipids has several advantages. First, the esterification process 610 reduces the levels of certain phosphorus and metals compounds present in algal oils. These materials are poisons to catalysts typically used in hydrotreating processes. Thus, esterification prior to hydrotreating prolongs the life of the hydrotreating catalyst. Also, esterification reduces the molecular weight of the compounds being hydrotreated, thereby improving the performance of the hydrotreating process 620. Further still, it is advantageous to retain the fuel esters from the distillation process 625 to be hydrotreated in a vaporous form, as doing so reduces the energy needed for hydrotreating.

In some embodiments of the invention, the neutral algal lipids are directly hydrotreated in order to convert the lipids into fuel products and additives. While in other implementations, the neutral lipids are esterified and separated into carotenoids, long chain unsaturated esters, eicosapentaenoic acid (EPA) esters, and/or fuel esters via distillation process 625. Distillation process 625 can include molecular distillation as well as any of the distillation techniques known in the art. For example, the distillates can be fractionated using a simple distillation column to separate the lower chain fatty acids for refining. The long chain unsaturated fatty acids remain as high boiling residue in the column. In some embodiments, the remaining vapor can then be sent to the hydrotreating process. Two of the advantages of the present invention are that it yields pure feed as well as a vapor product, which favors the energy intensive hydrotreating reaction, as described above.

In some embodiments of the invention, polar lipids (and, optionally, neutral lipids) are hydrolyzed in hydrolysis process 615 before being passed to the esterification process. Doing so unbinds the fatty acids of the algal lipids, and enables a greater amount of the algal lipids to be formed into useful products.

Figure 15:
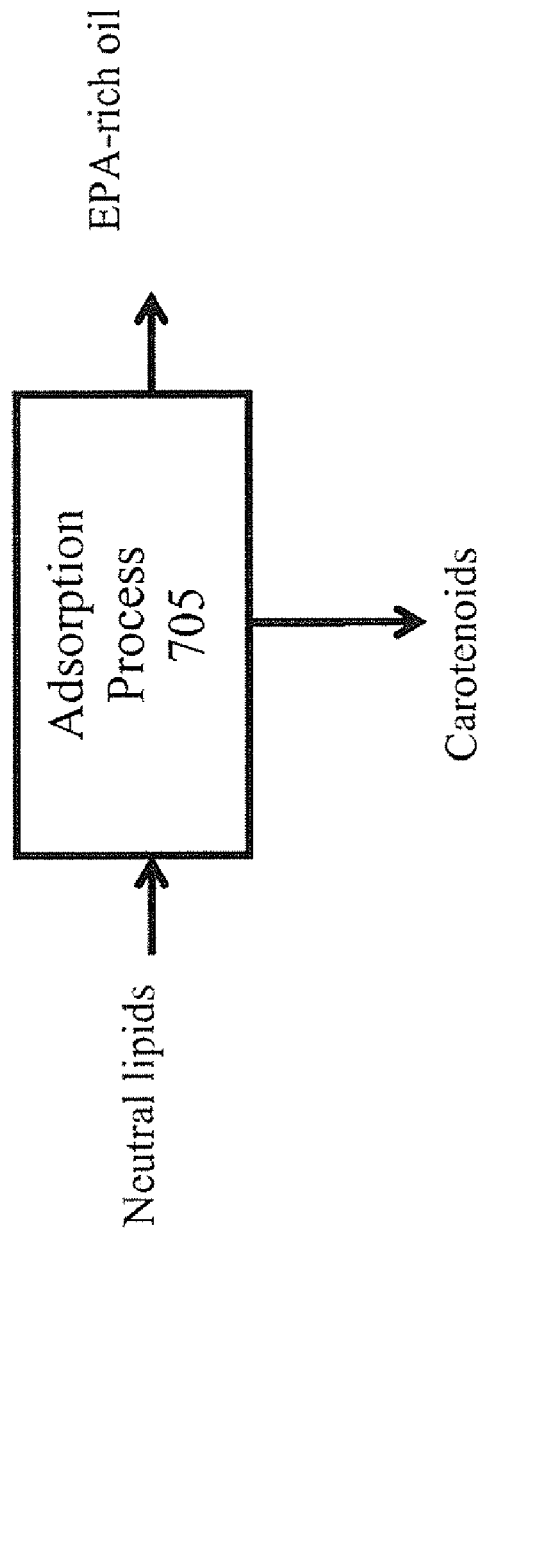
FIG. 15 is a flowchart describing one of the embodiments of the present invention wherein algae neutral lipids are processed to form various products.

FIG. 15 is a flowchart showing a process 700 for producing nutraceutical products from neutral lipids. In one implementation of process 700, neutral lipids are fed to an adsorption process 705 that separates carotenoids from EPA-rich oil. The neutral lipids can be from an algae source generated by any of the selective extraction techniques disclosed herein. However, the neutral lipids can be from other sources, such as plant sources.

Adsorption process 705 includes contacting the neutral lipids with an adsorbent to adsorb the carotenoids, such as beta carotene and xanthophylls. In one implementation, the adsorbent is Diaion HP20SS (commercially available from ITOCHU Chemicals America, Inc.). The neutral lipids can contact the adsorbent in a batch-type process, in which the neutral lipid and adsorbent are held in a vessel for a selected amount of time. After the contact time, the absorbent and liquid are separated using techniques known in the art. In other implementations, the adsorbent is held in an adsorbent bed, and the neutral lipids are passed through the adsorbent bed. Upon passing through the adsorbent bed, the carotenoids content of the neutral lipids is reduced, thereby producing an oil rich in EPA.

The carotenoids can be recovered from the adsorbent material by treating the adsorbent with an appropriate solvent, including, but not limited to, alcohols such as ethanol, isopropyl alcohol, butanol, esters such as ethyl acetate or butyl acetate, alkanes such as hexane, and pentane.

Figure 16:
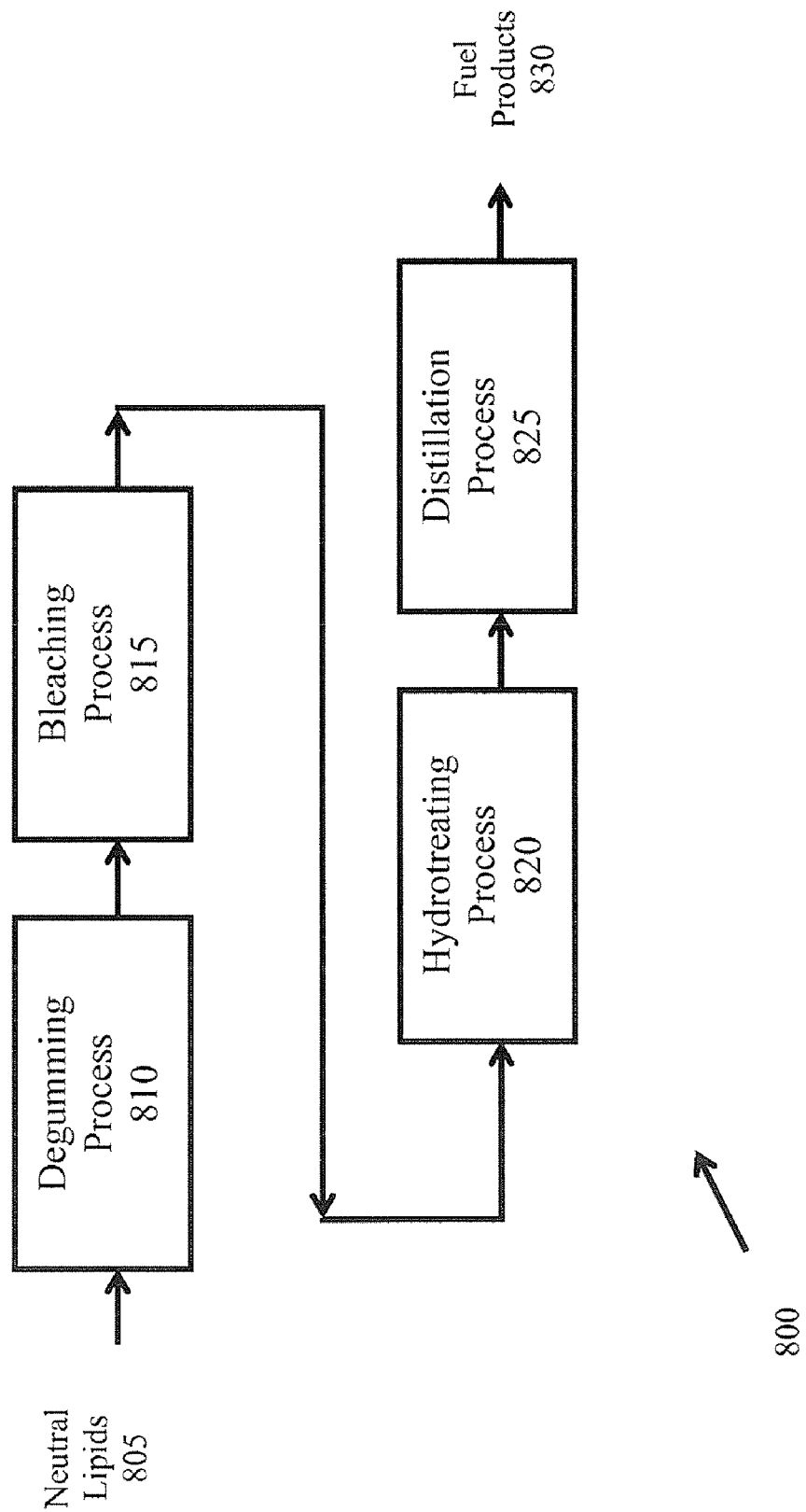
FIG. 16 is a flowchart describing one of the embodiments of the present invention wherein algae neutral lipids are processed to form fuel products.

FIG. 16 is a flowchart showing a process 800 for producing fuel products 830 from neutral lipids 805. The neutral lipids can be from an algae source generated by any of the selective extraction techniques disclosed herein. However, the neutral lipids can be from other sources, such as plant sources. The neutral lipids are treated in a degumming process 810, in which the lipids are acid washed to reduce the levels of metals and phospholipids in the neutral lipids. In some implementations, a relatively dilute solution of phosphoric acid is added to the neutral lipids, and the mixture is heated and agitated. The precipitated phospholipids and metals are then separated from the remaining oil, for example, by centrifuge.

The treated oil is then passed to bleaching process 815 to remove chlorophylls and other color compounds. In some implementations, bleaching process 815 includes contacting the oil with clay and or other adsorbent material such as bleaching clay (i.e. bentonite or fuller's earth), which reduce the levels of chlorophylls and other color compounds in the oil. The treated oil then is passed to hydrotreating process 820, which hydrogenates and deoxygenates the components of the oil to form fuels products, for example, jet fuel mixtures, diesel fuel additive, and propane. In addition, the hydrotreating process 820 also causes some cracking and the creation of smaller chain compounds, such as LPG and naptha. Any of the hydrotreating processes described herein can be used for hydrotreating process 820.

The mixture of compounds created in the hydrotreating process 820 are passed to a distillation process 825 to separate them into various fuel products 830. Distillation process 825 can include any of the molecular and non-molecular distillation techniques described herein or known in the art for separation of fuel compounds.

In some embodiments of the instant invention, proteins may be selectively extracted from an algal biomass. Extraction of proteins using the disclosed methods offers many advantages. In particular, algal cells do not need to be lysed prior to extracting the desired proteins. This simplifies and reduces costs of extraction. The methods of the instant invention exploit the solubility profiles of different classes of proteins in order to selectively extract and fractionate them from an algal culture, biomass, paste, or cake.

For example, an algal biomass may be subjected to heating and mixing to extract water and salt soluble proteins called albumins and globulins. This mixture can then be subjected to a change in pH to recover the alkali soluble proteins called the glutelins. This step can then be followed by a solvent-based separation of the alcohol soluble proteins called prolamins. The remaining biomass would be rich in carbohydrates and lipids.

Figure 17:
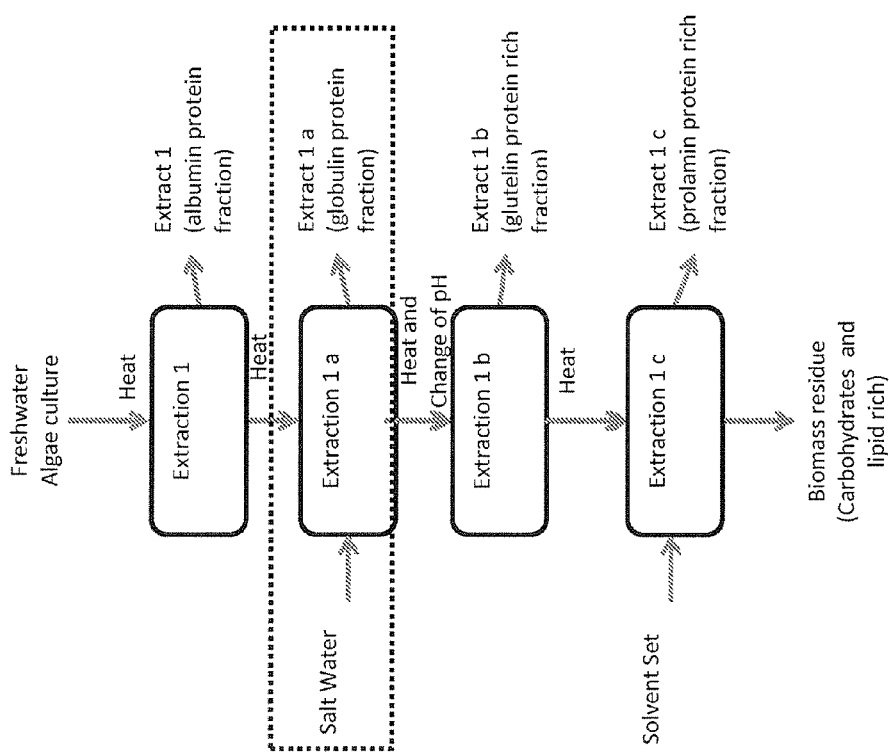
FIG. 17 is a flowchart describing one of the embodiments of the present invention wherein algae proteins are selectively extracted from a freshwater algal biomass.
Figure 18:
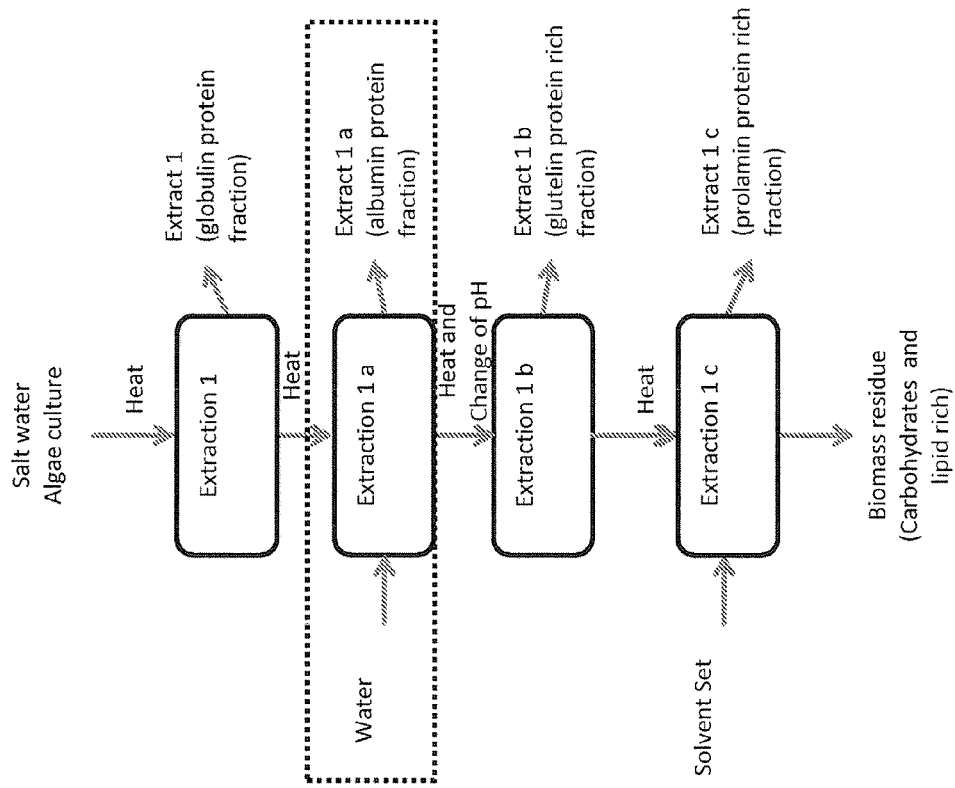
FIG. 18 is a flowchart describing one of the embodiments of the present invention wherein algae proteins are selectively extracted from a saltwater algal biomass.

Proteins can be extracted from both saltwater and freshwater algal cells, as shown in FIGS. 17 and 18. The presence of salt in the saltwater algal culture or biomass affects the extraction of different classes of protein, but the methods disclosed herein enable one to selectively extract proteins from either fresh or saltwater algae.

In some embodiments, extraction of proteins from freshwater algal cells is accomplished by the novel process shown in FIG. 17. Freshwater algal cells or a freshwater algal biomass are heated and mixed. Mixing can be accomplished by a variety of methods known in the art such as, but not limited to, stirring, agitation, and rocking. This process generates a first heated extraction mixture or slurry, comprised of a first substantially liquid phase and a first substantially solid phase. The solid and liquid phases are then separated. Separation can be accomplished by a variety of methods known in the art including, but not limited to, centrifugation, decantation, flotation, sedimentation, and filtration. This first substantially liquid phase is enriched in albumin proteins.

The first substantially solid phase is then mixed with salt water and heated to generate a second heated extraction mixture or slurry, comprised of a second substantially liquid phase and a second substantially solid phase. The salt water may be natural seawater or may be an aqueous salt solution. An example of such a solution would comprise about typically 35 g/L comprising mainly of NaCl. The solid and liquid phases are then separated. This second substantially liquid phase is enriched in globulin proteins.

The second substantially solid phase is then mixed with water and heated to generate a third heated extraction mixture or slurry, comprised of a third substantially liquid phase and a third substantially solid phase. The pH of this third extraction mixture or slurry is then raised to about 9 or greater, enriching the third substantially liquid phase with glutelin proteins. The solid and liquid phases are then separated, the third substantially liquid phase being enriched in glutelin proteins.

The third substantially solid phase is then mixed with a solvent set and heated to generate a fourth heated extraction mixture or slurry, comprised of a fourth substantially liquid phase and a fourth substantially solid phase. In one preferred embodiment, the solvent set comprises ethanol. In other non-limiting embodiments, the solvent set comprises one or more of the following solvents: methanol, isopropanol, acetone, ethyl acetate, and acetonitrile. The solid and liquid phases are then separated. This fourth substantially liquid phase is enriched in prolamin proteins. The remaining fourth substantially solid phase may be enriched in lipids, depending on the composition of the starting algal biomass.

In some embodiments, extraction of proteins from saltwater algal cells is accomplished by the novel process shown in FIG. 18. Saltwater algal cells or a saltwater algal biomass are heated and mixed. Mixing can be accomplished by a variety of methods known in the art such as, but not limited to, stirring, agitation, and rocking. This process generates a first heated extraction mixture or slurry, comprised of a first substantially liquid phase and a first substantially solid phase. The solid and liquid phases are then separated. Separation can be accomplished by a variety of methods known in the art including, but not limited to, centrifugation, decantation, flotation, sedimentation, and filtration. This first substantially liquid phase is enriched in globulin proteins.

The first substantially solid phase is then mixed with water and heated to generate a second heated extraction mixture or slurry, comprised of a second substantially liquid phase and a second substantially solid phase. The solid and liquid phases are then separated. This second substantially liquid phase is enriched in albumin proteins.

The second substantially solid phase is then mixed with water and heated to generate a third heated extraction mixture or slurry, comprised of a third substantially liquid phase and a third substantially solid phase. The pH of this third extraction mixture or slurry is then raised to pH 9 or greater, enriching the third substantially liquid phase with glutelin proteins. The solid and liquid phases are then separated, the third substantially liquid phase being enriched in glutelin proteins.

The third substantially solid phase is then mixed with a solvent set and heated to generate a fourth heated extraction mixture or slurry, comprised of a fourth substantially liquid phase and a fourth substantially solid phase. In one preferred embodiment, the solvent set comprises ethanol. In other non-limiting embodiments, the solvent set comprises one or more of the following solvents: methanol, isopropanol, acetone, ethyl acetate, and acetonitrile. The solid and liquid phases are then separated. This fourth substantially liquid phase is enriched in prolamin proteins. The remaining fourth substantially solid phase may be enriched in lipids, depending on the composition of the starting algal biomass.

The disclosed methods also provide for the selective extraction of different types of proteins, as shown in FIGS. 17-20. Any of the steps of the aforementioned extraction process can be performed separately from the rest of the steps in order to selectively extract a single protein product. Two examples of this appear in FIGS. 17 and 18, as the as demonstrated by the dashed box around extraction step 1*a*.

In a non-limiting example, globulin proteins can be selectively extracted from a freshwater algal biomass by mixing said biomass with salt water and heating to generate a heated extraction mixture or slurry, comprised of a substantially liquid phase and a substantially solid phase. The solid and liquid phases can then be separated. The liquid phase is enriched in globulin proteins. See FIG. 17, extraction step 1*a*.

In another non-limiting example, albumin proteins can be selectively extracted from a saltwater algal biomass by mixing said biomass with water and heating to generate a heated extraction mixture or slurry, comprised of a substantially liquid phase and a substantially solid phase. The solid and liquid phases can then be separated. The liquid phase is enriched in globulin proteins. See FIG. 18, extraction step 1*a*.

Figure 19:
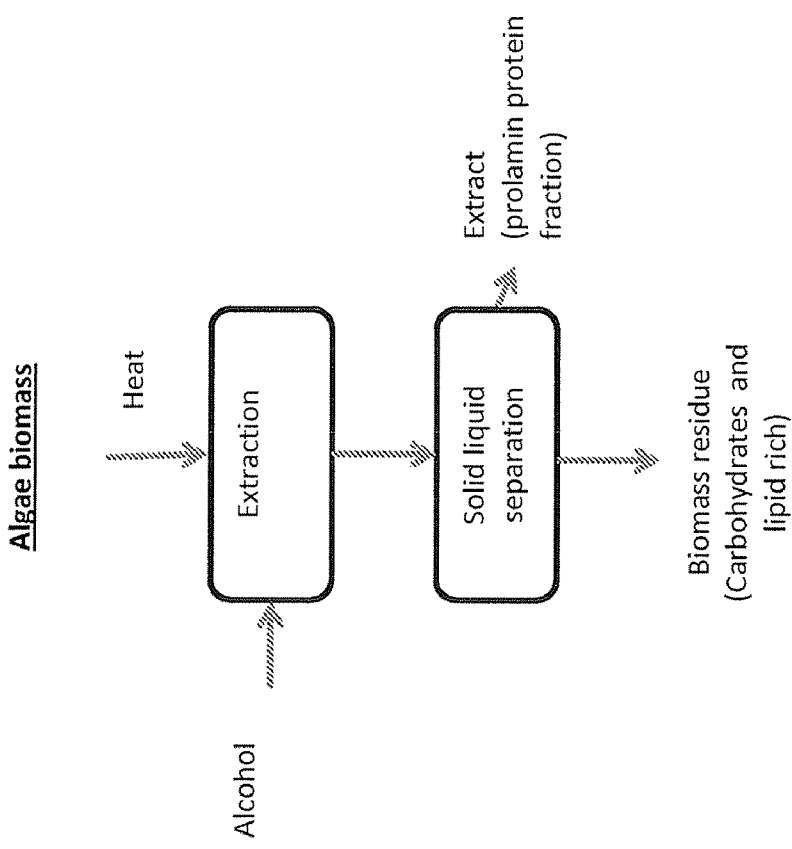
FIG. 19 is a flowchart describing one of the embodiments of the present invention wherein a selected algae protein is extracted from a saltwater or freshwater algal biomass.

In a further non-limiting example, prolamin proteins can be selectively extracted from either a freshwater or saltwater algal biomass as shown in FIG. 19. The selective extraction is accomplished by mixing the algal biomass with a solvent set and heating to generate a heated extraction mixture or slurry, comprised of a substantially liquid phase and a substantially solid phase. The solid and liquid phases can then be separated. The liquid phase is enriched in prolamin proteins.

Figure 20:
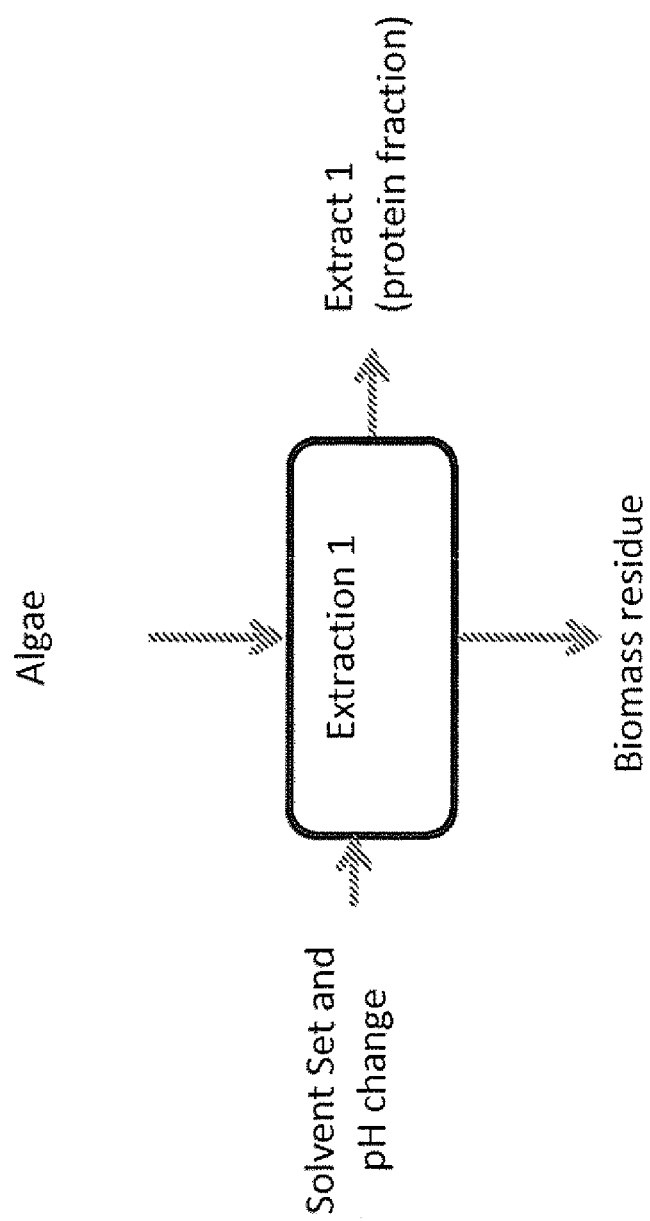
FIG. 20 is a flowchart describing one of the embodiments of the present invention wherein a selected algae protein is extracted from a saltwater or freshwater algal biomass.
Figure 21:
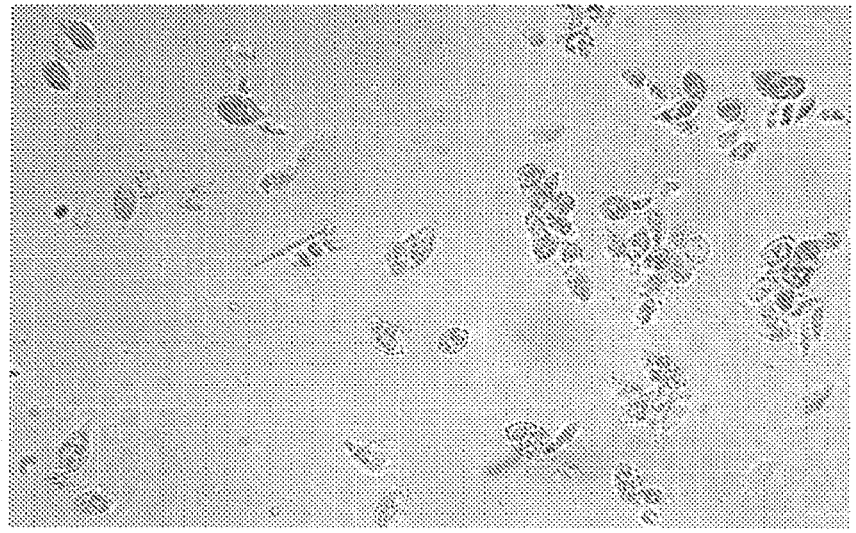
FIG. 21 is a photograph showing *Scenedescemus* sp. cells before and after extraction using the methods described herein. The cells are substantially intact both before and after extraction.
Figure 21:
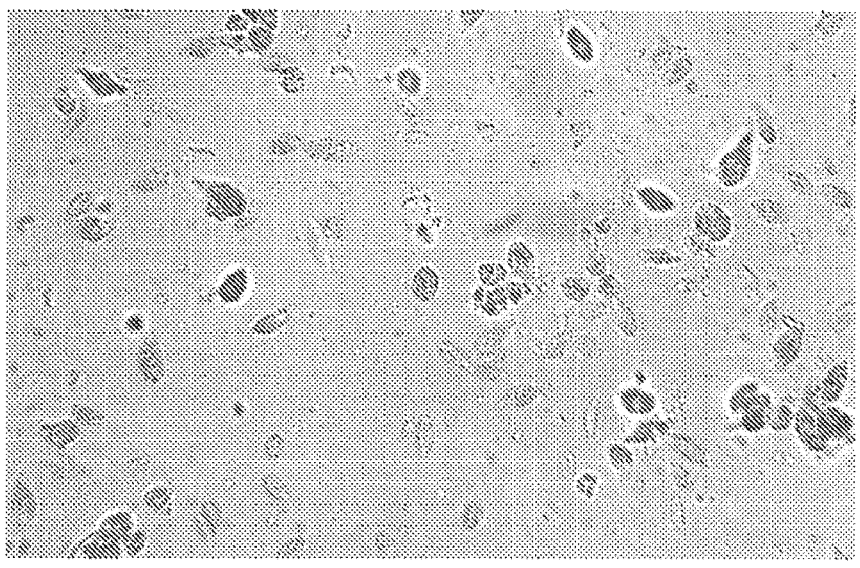

In yet another non-limiting example, a protein fraction can be selectively extracted from either a freshwater or saltwater algal biomass as shown in FIG. 20. The selective extraction is accomplished by mixing the algal biomass with a solvent set to generate an extraction mixture or slurry and effecting a pH change in the mixture. The mixture is comprised of a substantially liquid phase and a substantially solid phase. The solid and liquid phases can then be separated. The liquid phase is enriched in proteins Having been informed of these aspects of the invention, one of skill in the art would be able to selectively extract a desired protein from either a freshwater or saltwater algal biomass by either a single step extraction process, or a multi-step extraction process. In light of the instant disclosure, one of skill in the art would be able to interchange the order of the above disclosed multi-step extraction schemes, provided that the protein content of the algal mass and the solubility properties of the proteins of interest are taken into account. Other embodiments of the disclosed methods may incorporate a wash step between each extraction step.

For any of the disclosed protein extraction methods, the extraction mixture/slurry may be maintained at a heated temperature for a period of time. In some embodiments, the extraction mixture is maintained at a heated temperature for between about 20 minutes to about 90 minutes. In some aspects, the extraction mixture is maintained at a heated temperature for between about 20 minutes and about 60 minutes. In other aspects, the extraction mixture is maintained at a heated temperature for between about 45 minutes to about 90 minutes.

In some embodiments, the extraction mixture/slurry may be heated to temperatures less than about 50° C. In some aspects, the albumin, globulin, and glutelin proteins are extracted at temperatures of less than about 50° C. In other embodiments the extraction mixture/slurry is heated to a temperature close to the boiling point of extraction mixture/slurry. In some aspects, the prolamin proteins are extracted at temperatures close to the boiling point of the extraction mixture/slurry. In other embodiments, the pressure is increased above atmospheric pressure, up to and including, 50 psi, during the heating and mixing steps to enhance extraction Example 1

Green microalgae *Scendesmus dimorphus* (SD) were cultured in outdoor panel photobioreactors. SD samples of varying lipid contents were harvested. After removal of bulk water by centrifugation, the algal samples were stored as 3-5 cm algae cakes at −80° C. until use. A pre-calculated amount of wet algal biomass (15 grams dry algae weight equivalent) and 90 mL of ethanol solvent was added into a three-neck flask equipped with condenser, mechanical stirring and a thermocouple. In one experiment, the mixture was refluxed for 10 min under microwave irradiance. In a second, the mixture was refluxed for 1 h with electronic heating. Afterwards, the mixture was cooled to room temperature and separated into a diffusate and retentate by filtration.

The total lipids of algal samples were analyzed using a chloroform-methanol-water system according to Bligh and Dyer's lipid extraction method. This total lipid value was used as reference for the lipid recovery calculation. Total lipids were further separated into neutral lipids and polar lipids by standard column chromatography method using 60-200 mesh silica gel (Merck Corp., Germany). Each lipid fraction was transferred into a pre-weighed vial, initially evaporated at 30° C. using a rotary evaporator (Büchi, Switzerland) and then dried under high vacuum. The dried retentates were placed under nitrogen and then weighed. The fatty acid profile of each sample was quantified by GC-MS after derivatization into fatty acid methyl esters using heptadecanoic acid (C17:0) as the internal standard.

The results (data not shown) indicated that microwave assisted extraction was best for removal of the polar lipids in the first extraction step, and somewhat less effective for the separation of neutral lipids. Electronic heating is more consistent in extraction effectiveness. The final yield is comparable between microwave assisted extraction and electronic heating assisted extraction, but, microwave assisted extraction is significantly faster.

Example 2

Protein Extraction from Algal Biomass (1) Acid Leaching: Algal biomass was soaked in water at pH 4.5 for 1 hour. The samples were then centrifuged at 3000 rpm for three minutes, and the supernatant removed. The remaining solids were washed 3 times with dilute acid (pH 4.5) and freeze dried.

(2) Alkaline extraction: Algal biomass was soaked in water at pH 11 for 1 hour. following the addition of pH-adjusted water. The samples were then centrifuged at 3000 rpm for three minutes, and the supernatant removed. The supernatant was neutralized with acid (pH 4.5) following the centrifugation. The remaining solids were washed 3 times with dilute acid (pH 4.5) and freeze dried.

The results of acid leaching and alkaline extraction are shown below in Table 4.

TABLE 4

| Process | Protein Yield (% weight) | Protein Purity (% weight of protein yield) |
|---|---|---|
| Alkaline Extraction | 16 | 45 |
| Acid Leaching | 70 | 32.5 |

Protein yield was calculated on a weight basis, comparing the weight of the freeze dried solids to the weight of the algal biomass prior to soaking in pH-adjusted water. Protein purity was determined by the Official Method of the American Oil Chemists' Society (Ba-2a-38), measuring the amount of nitrogen in the freeze dried solids of each process. As proteins are an important product that adds to the value of algal product extraction, this information allows for the use of feedstocks with varying levels of protein in the systems and methods disclosed herein.

Example 3

Extraction of Proteins from Saltwater Algal Biomass

The saltwater algal culture initially made up of about 1-10% w/w solids in saltwater was heated to 50° C. and maintained at this temperature for 1 hr. The resulting slurry was centrifuged to separate the liquid phase from the solid phase. The liquid extract was determined to be rich in globulin proteins (about 10% of the total proteins present in the original algal biomass).

The solids were then suspended in fresh water and heated to about 50° C. and maintained for about 1 hour. The resulting slurry was centrifuged again to separate the liquid from the solid phase. The liquid phase was determined to be rich in albumin proteins (about 10% of the total proteins present in the original algal biomass).

The solids were then suspended in ethanol to achieve a 70% w/w mixture. This mixture was heated to about 75° C. and maintained at that temperature for about 1 hour. The resulting slurry was centrifuged to separate the liquid from the solid phase. The liquid phase was determined to be rich in albumin proteins (about 30% of the total proteins present in the original biomass).

The solids were then suspended in alkali solution (aqueous NaOH, pH 9) and heated to about 50° C. and maintained at that temperature for about 1 hour. The resulting slurry was centrifuged to separate the liquid from the solid phase. The liquid phase was determined to be rich in glutelin proteins (about 50% of the total proteins present in the original biomass).

Example 4

Step Fractionation and Extraction of Algal Biomass by Ethanol

One thousand pounds of *Nannochloropsis* biomass (cultured from strain 202.0, obtained from Arizona State University, Laboratory for Algae Research and Biotechnology, ATCC Deposit Number PTA-11048), was harvested and dewatered until algae comprised about 35% w/w and then finally frozen.

The extraction steps were performed in a 400 gallon jacketed kettle with hinged lids. The lids were tied down with straps and sealed with silicone. The system also contained a mixer with a 2 horsepower explosion proof motor with a two blade shaft. The frozen algae material was emptied into the tank and an equal weight of ethanol was pumped in using a pneumatic drum pump. The material was stirred for 15 minutes and the jacket heated with steam to obtain the desired temperature at each extraction step. The desired temperature is near, meaning within 3° C. of the boiling point of the mixture, but not boiling. This desired temperature is different at each extraction step as the boiling point of the mixture changes as the proportion of ethanol is changed. Upon reaching the desired temperature, the system was stirred continuously held at the desired temperature for 60 minutes to ensure that the contents of the kettle were uniformly heated.

The contents of the kettle were then pumped out of the extraction vessel and into a Sharples decanter centrifuge, using a pneumatic Viking vane pump at about 1 gallon per minute. The decanter centrifuge rotor speed was set to about 6000 rpm. The solids were collected in an enclosed plastic drum and consisted of about 50% w/w solids to liquids. These solids were returned to the kettle, where the aforementioned extraction steps were repeated. The liquid stream from the decanter was collected into a feed tank was and then fed to the membrane filtration system. The membrane used was a 0.375 ft$^2$ SS membrane manufactured by Graver Technologies. The operating conditions were 60° C.±5° C. and with an average pressure gradient of 40 psi. The membrane system was backwashed about every 15 minutes with compressed air to maintain the flux. The permeate collected from the membrane system was free of any particulate matter. The retentate was collected and recycled to the decanter.

This extraction and fractionation is due to the change in polarity of the solvent through the process in each extraction. In the extraction shown in FIG. 13, the process began with about 1000 lbs. of wet algal biomass containing about 65% pure water (35% w/w algal solids). This was mixed with 860 lbs. of denatured ethanol (95% ethanol and 5% methanol), resulting in a mixture containing about 55% aqueous ethanol. The solids and liquids were separated using a decanter as described above. The wet solid portion weighed 525 lbs. and was 40% dry mass. A total of 525 lbs. of 95% the denatured ethanol was added to the solids, resulting in a mixture made up of about 85% aqueous ethanol. The solids and liquids were separated using a decanter as described above. The solid portion weighed 354.5 lbs. and was 40% dry mass. To this mass, another 700 lbs. of denatured ethanol was added, resulting in a mixture of about 95% aqueous ethanol. The solids and liquids were separated using a decanter as described above. The resulting solids were about 40% dry mass. This biomass requires 60% less energy to dry, calculated based on the latent heat of water and ethanol.

In some experiments (data not shown) other types of denatured ethanol were tried. Denatured ethanol containing 95% ethanol and 5% isopropyl alcohol was used in an extraction, but was found not to be as effective as 95% ethanol and 5% methanol. Use of 100% ethanol is a preferred embodiment of the present invention, but is generally not available due to cost constraints.

Figure 13:
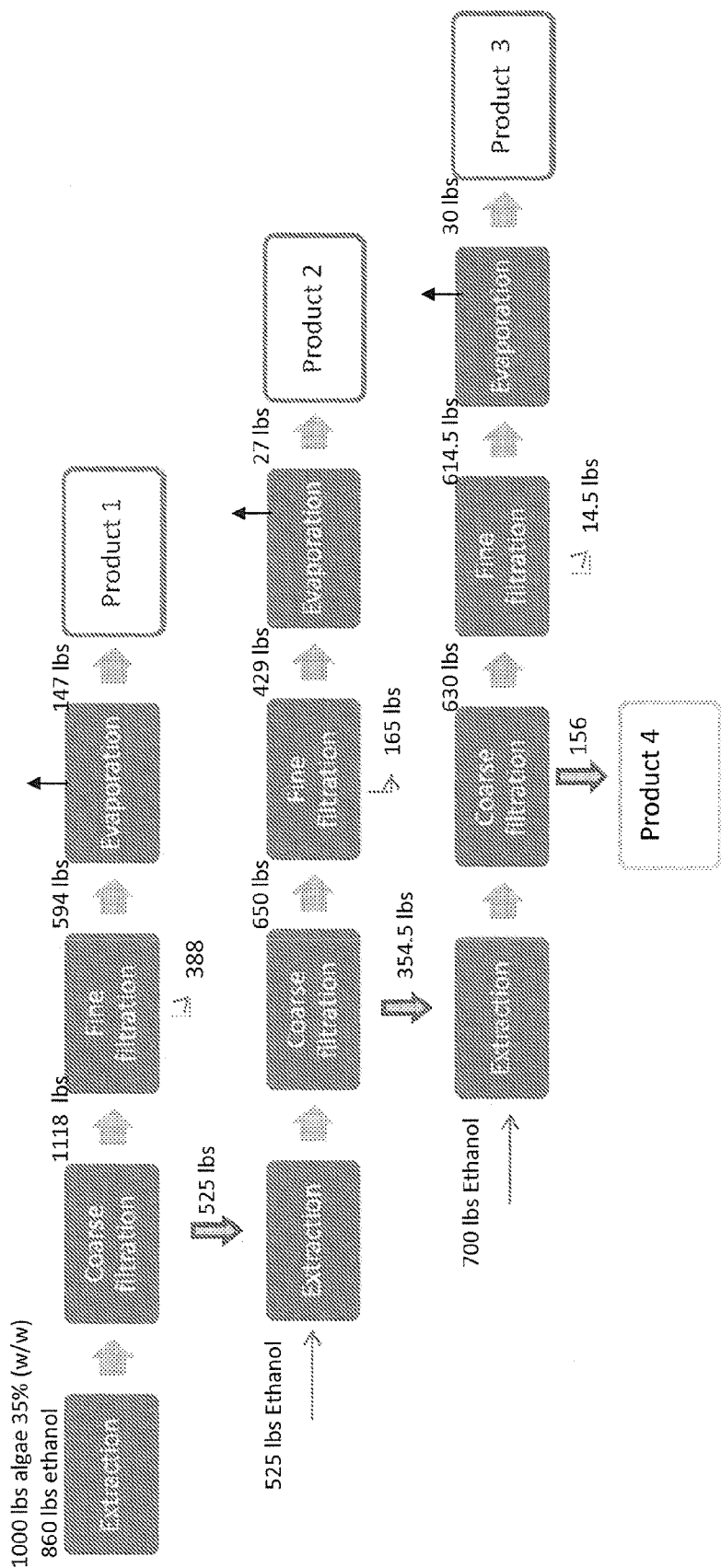
FIG. 13 is a flowchart and mass balance diagram describing one of the embodiments of the present invention wherein 1000 lbs. of algal biomass was processed through extraction and fractionation in order to separate neutral lipids, polar lipids, and protein from the algal biomass.

The permeate stream from the membrane system was evaporated using an in-house fabricated batch still. The operating conditions were about 80° C. during the vacuum distillation. All of the ethanol in the permeate was evaporated. These extraction steps were repeated three times, resulting in four product pools, as shown in FIG. 13. This is because with each extraction step, the polarity changed with the addition of water to the mixture, allowing for the extraction of different components with each step. Product 1 contained the algal proteins, and as a result, retained excess water in the system that could not be vaporized under the operating conditions. Product 2 contained the polar lipids. Product 3 contained the neutral lipids. Finally, Product 4 was the residual biomass, containing potential coproducts such as carotenoids.

Example 5

Dewatering and Extraction of Algal Biomass by Ethanol

Upon harvesting, algal biomass typically contains between about 0.1 to 0.5% (w/w) solids. This can be dewatered using any of the methods known in the algae industry, including, but not limited to membrane filtration, centrifugation, heating, sedimentation or flotation. Flocculation can either assist in flotation or sedimentation. The typical result of such methods is an algae slurry containing about 10% w/w solids. To dewater further, another dewatering method may be used to remove some of the remaining free water to get the concentration of solids closer to 40% w/w. However, the cost of dewatering increases exponentially after the first dewatering is carried out. An advantage of the systems and methods disclosed herein is that the allow for the extraction and fractionation of an algal mass that has undergone only one round of dewatering.

An example of such a process might be that in the first extraction round, following the protocol described in Example 3, 1000 lbs. of wet biomass containing 90% pure water and is mixed with 1000 lbs. of denatured ethanol (95% EtOH and 5% MeOH), resulting in a solvent mixture of about 50% aqueous ethanol. The resulting biomass (350 lbs.) is 40% dry. The solvent composition of these wet solids is 50% aqueous ethanol. With another 350 lbs. of denatured ethanol, the composition of the mixture would be about 81% aqueous ethanol. The resulting biomass (235 lbs.) is 40% dry. The solvent composition of these wet solids is 81% aqueous ethanol. With another 470 lbs. of denatured ethanol, the composition of the mixture would be about 95% aqueous ethanol. The resulting solids would be 40% dry with about 95% ethanol. This wet biomass requires 60% less energy to dry based on the latent heat of water and ethanol. In this case, 100 lbs. of algae would have been extracted using 1820 lbs. ethanol. When compared with Example 3, wherein the starting material was 40% algal solids, 350 lbs. of the dry algae equivalent was extracted with 2085 lbs. ethanol.

REFERENCES

The following references are herein incorporated by reference in their entirety:

U.S. Pat. No. 7,148,366

Rhodes, *Science Progress*, 92(1):39-90, 2009. Generic review on using algae to produce biodiesel Chisti, Y. (2007). Biodiesel from microalgae. *Biotechnol Adv* 25, 294-306. Generic review on using algae to produce biodiesel Amin, *Energy Convers. Manage.*, 50:1834-1840, 2009. Generic review on using algae to produce biofuel and gas Catchpole et al., J. of Supercritical Fluids, 47:591-597, 2009. SCF CO2 based extraction of specialty lipids Bligh E G & Dyer W J. A rapid method of total lipid extraction and purification. Can. J. Biochem. Physiol. 37: 911-917, 1959.

Christie, W. W, *Lipid Analysis*, 3rd ed., Oily Press, Bridgewater, UK, 2003, 416.

Approved Methods of the AACC, 9th ed., American Association of Cereal Chemists. St. Paul, Minn., 1995 AACC Method 58-19.

The invention claimed is:

1. A method of isolating carotenoids and omega-3 rich oil from algae, comprising:
    dewatering intact algal cells to make a wet algal biomass;
    adding a first alcohol fraction to the wet algal biomass in a ratio of about 1 part alcohol to about 1 part algal biomass by weight;
    separating a first solid biomass fraction from a first liquid fraction comprising proteins;
    combining the first solid biomass fraction with a second alcohol fraction in a ratio of about 1 part alcohol to about 1 part solids by weight;
    separating a second solid biomass fraction from a second liquid fraction comprising polar lipids;
    combining the second solid biomass fraction with a third alcohol solvent fraction in a ratio of about 1 part alcohol to about 1 part solid biomass by weight;
    separating a third solid biomass fraction from a third liquid fraction comprising neutral lipids, wherein the third solid biomass fraction comprises carbohydrates, and wherein the first liquid fraction has a higher protein concentration than the second and third liquid fractions, the second liquid fraction has a higher polar lipids concentration than the first and third liquid fractions, and the third liquid fraction has a higher neutral lipids concentration than the first and second liquid fractions; and
    separating the neutral lipids into carotenoids and omega-3 rich oil.

2. The method of claim 1, further comprising isolating carotenoids, omega-3 rich oil, carbohydrates and polar lipids.

3. The method of claim 1, further comprising isolating the polar lipids from components that are not polar lipid components.

4. The method of claim 1, further comprising processing the polar lipids into at least one of lubricants, detergents, and food additives.

5. The method of claim 1, further comprising isolating carotenoids from non-carotenoid components.

6. The method of claim 1, wherein at least one of the first, second, and third solvent sets is comprised of ethanol.

7. A method of isolating carotenoids and omega-3 rich oil from algae, comprising:
    dewatering intact algal cells to make a wet algal biomass;
    adding a first alcohol fraction to the wet algal biomass in a ratio of about 1 part alcohol to about 1 part algal biomass by weight;
    separating a first solid biomass fraction from a first liquid fraction comprising proteins;
    combining the first solid biomass fraction with a second alcohol fraction in a ratio of about 1 part alcohol to about 1 part solids by weight;
    separating a second solid biomass fraction from a second liquid fraction comprising polar lipids;
    combining the second solid biomass fraction with a third alcohol solvent fraction in a ratio of about 1 part alcohol to about 1 part solid biomass by weight;
    separating a third solid biomass fraction from a third liquid fraction comprising neutral lipids, wherein the third solid biomass fraction comprises carbohydrates, and wherein the first liquid fraction is more polar than the second and third liquid fractions, the second liquid fraction is less polar than the first fraction, but more polar than the third fraction, and the third fraction is less polar than the first and second liquid fractions; and
    separating the neutral lipids into carotenoids and omega-3 rich oil.

8. A method of isolating carotenoids and omega-3 rich oil from algae, comprising:
    dewatering intact algal cells to make a wet algal biomass;
    adding a first alcohol fraction to the wet algal biomass in a ratio of about 1 part alcohol to about 1 part algal biomass by weight;
    separating a first solid biomass fraction from a first liquid fraction comprising proteins;
    combining the first solid biomass fraction with a second alcohol fraction in a ratio of about 1 part alcohol to about 1 part solids by weight;
    separating a second solid biomass fraction from a second liquid fraction comprising polar lipids;
    combining the second solid biomass fraction with a third alcohol solvent fraction in a ratio of about 1 part alcohol to about 1 part solid biomass by weight;
    separating a third solid biomass fraction from a third liquid fraction comprising neutral lipids, wherein the third solid biomass fraction comprises carbohydrates, and wherein the first liquid fraction contains more water than the second and third liquid fractions, the second liquid fraction contains less water than the first fraction, but more water than the third fraction, and the third fraction contains less water than the first and second liquid fractions; and
    separating the neutral lipids into carotenoids and omega-3 rich oil.

* * * * *